(12) United States Patent
Schneider et al.

(10) Patent No.: US 12,150,381 B2
(45) Date of Patent: Nov. 19, 2024

(54) N-TYPE DOPANTS FOR EFFICIENT SOLAR CELLS

(71) Applicant: THE REGENTS OF THE UNIVERSITY OF CALIFORNIA, Oakland, CA (US)

(72) Inventors: Julia Schneider, New Haven, CT (US); Michael L. Chabinyc, Santa Barbara, CA (US); Hengbin Wang, Santa Barbara, CA (US); Hidenori Nakayama, Goleta, CA (US); Kyle D. Clark, Santa Barbara, CA (US); Javier Read de Alaniz, Santa Barbara, CA (US)

(73) Assignees: THE REGENTS OF THE UNIVERSITY OF CALIFORNIA, Oakland, CA (US); THE MITSUBISHI CHEMICAL CORPORATION, Tokyo (JP)

(*) Notice: Subject to any disclaimer, the term of this patent is extended or adjusted under 35 U.S.C. 154(b) by 64 days.

(21) Appl. No.: 17/826,455

(22) Filed: May 27, 2022

(65) Prior Publication Data
US 2022/0293866 A1 Sep. 15, 2022

Related U.S. Application Data

(62) Division of application No. 16/712,206, filed on Dec. 12, 2019, now Pat. No. 11,380,852.
(Continued)

(51) Int. Cl.
H10K 85/60 (2023.01)
B82Y 30/00 (2011.01)
(Continued)

(52) U.S. Cl.
CPC .......... *H10K 85/6572* (2023.02); *B82Y 30/00* (2013.01); *C07D 487/12* (2013.01);
(Continued)

(58) Field of Classification Search
CPC ............. H01L 51/0072; H01L 51/0047; H01L 51/4253; H01L 51/005; H01L 51/5076;
(Continued)

(56) References Cited

U.S. PATENT DOCUMENTS

2011/0309340 A1    12/2011  Schmid et al.
2018/0375037 A1    12/2018  Chen et al.
(Continued)

FOREIGN PATENT DOCUMENTS

CN    102731766 A    * 10/2012
WO    2016181705 A1    11/2016
(Continued)

OTHER PUBLICATIONS

Bendikov et al., "Tetrathiafulvalenes, Oligoacenenes, and Their Buckminsterfullerene Derivatives: The Brick and Mortar of Organic Electronics". Chem. Rev. 2004, 104, pp. 4891-4945.
(Continued)

*Primary Examiner* — Tri V Nguyen
(74) *Attorney, Agent, or Firm* — GATES & COOPER LLP

(57) ABSTRACT

Triazabicylodecene can effectively n-dope a variety of organic semiconductors, including PCBM, thus increasing in-plane conductivities. We synthesized a series of TBD-based n-dopants via an N-alkylation reaction and studied the effect of various alkyl chains on the physical and device properties of the dopants. Combining two TBD moieties on a long alky chain gave a solid dopant, 2TBD-C10, with high thermal stability above 250° C. PCBM films doped by 2TBD-C10 were the most tolerant to thermal annealing and
(Continued)

reached in-plane conductivities of $6.5 \times 10^{-2}$ S/cm. Furthermore, incorporating 2TBD-C10 doped PCBM as the electron transport layer (ETL) in methylammonium lead triiodide (MAPbI$_3$) based photovoltaics led to a 23% increase in performance, from 11.8% to 14.5% PCE.

15 Claims, 27 Drawing Sheets

Related U.S. Application Data

(60) Provisional application No. 62/778,685, filed on Dec. 12, 2018.

(51) Int. Cl.
*C07D 487/12* (2006.01)
*C07D 487/16* (2006.01)
*H01B 1/04* (2006.01)
*H10K 30/30* (2023.01)
*H10K 85/20* (2023.01)

(52) U.S. Cl.
CPC ......... *C07D 487/16* (2013.01); *H10K 85/215* (2023.02); *H01B 1/04* (2013.01); *H10K 30/30* (2023.02)

(58) Field of Classification Search
CPC .. Y02E 10/549; C07D 487/12; C07D 487/16; H01B 1/04; B82Y 30/00; H10K 2102/351; H10K 50/13; H10K 50/17; H10K 50/81; H10K 50/82; H10K 50/155; H10K 50/165; H10K 50/166; H10K 50/181; H10K 50/85; H10K 50/615; H10K 50/654; H10K 50/6572
USPC ........... 136/263; 257/40; 977/742, 734, 735, 977/773, 932
See application file for complete search history.

(56) References Cited

U.S. PATENT DOCUMENTS

| | | |
|---|---|---|
| 2019/0027700 A1 | 1/2019 | Shimizu et al. |
| 2019/0081239 A1 | 3/2019 | Fukagawa et al. |
| 2020/0035925 A1 | 1/2020 | Isogai et al. |

FOREIGN PATENT DOCUMENTS

| | | |
|---|---|---|
| WO | 2017130836 A1 | 8/2017 |
| WO | 2018180146 A1 | 10/2018 |

OTHER PUBLICATIONS

Foster et al., "Electron Collection as a Limit to Polymer:PCBM Solar Cell Efficiency: Effect of Blend Microstructure on Carrier Mobility and Device Performance in PTB7:PCBM". Adv. Energy Mater. 2014, 4, 1400311, pp. 1-12.
Ganesamoorthy et al., "Review: Fullerene based acceptors for efficient bulk heterojunction organic solar cell applications". Solar Energy Materials & Solar Cells 161 (2017) pp. 102-148.
Hu et al., "An Amidine-Type n-Dopant for Solution-Processed Field-Effect Transistors and Perovskite Solar Cells". Adv. Funct. Mater. 2017, 27, 1703254, pp. 1-9.
Klos et al., "Doping of C60 with tertiary amines: TDAE, DBU, DBN. A comparative study". Chemical Physics Letters 224 (1994) pp. 333-337.
Li et al., "Leuco Crystal Violet as a Dopant for n-Doping of Organic Thin Films of Fullerene C60". J. Phys. Chem. B 2004, 108, pp. 17076-17082.
Lussem et al., "Doped Organic Transistors". Chem. Rev. 2016, 116, pp. 13714-13751.
Naab et al., "Effective Solution- and Vacuum-Processed n-Doping by Dimers of Benzimidazoline Radicals". Adv. Mater. 2014, 26, pp. 4268-4272.
Perry et al., "N-Type Surface Doping of MAPbI3 via Charge Transfer from Small Molecules". Adv. Electron. Mater. 2018, 4, 1800087, pp. 1-7.
Russ et al., "Power Factor Enhancement in Solution-Processed Organic n-Type Thermoelectrics Through Molecular Design". Adv. Mater. 2014, 26, pp. 3473-3477.
Skiebe et al., "[DBU]C60. Spin pairing in a fullerene salt". Chemical Physics Letters 220 (1994) pp. 138-140.
Yan et al., "Non-fullerene acceptors for organic solar cells". Nature Reviews, Materials, vol. 3 | Article No. 18003, 2018, pp. 1-19.
Yang et al., "Side-Chain Isomerization on an n-type Organic Semiconductor ITIC Acceptor Makes 11.77% High Efficiency Polymer Solar Cells". J. Am. Chem. Soc. 2016, 138, pp. 15011-15018.
Final Office Action dated Sep. 16, 2021 for U.S. Appl. No. 16/712,206.
Non-Final Office Action dated Dec. 31, 2020 for U.S. Appl. No. 16/712,206.
Notice of Allowance and Fees due dated Mar. 3, 2022 for U.S. Appl. No. 16/712,206.

\* cited by examiner

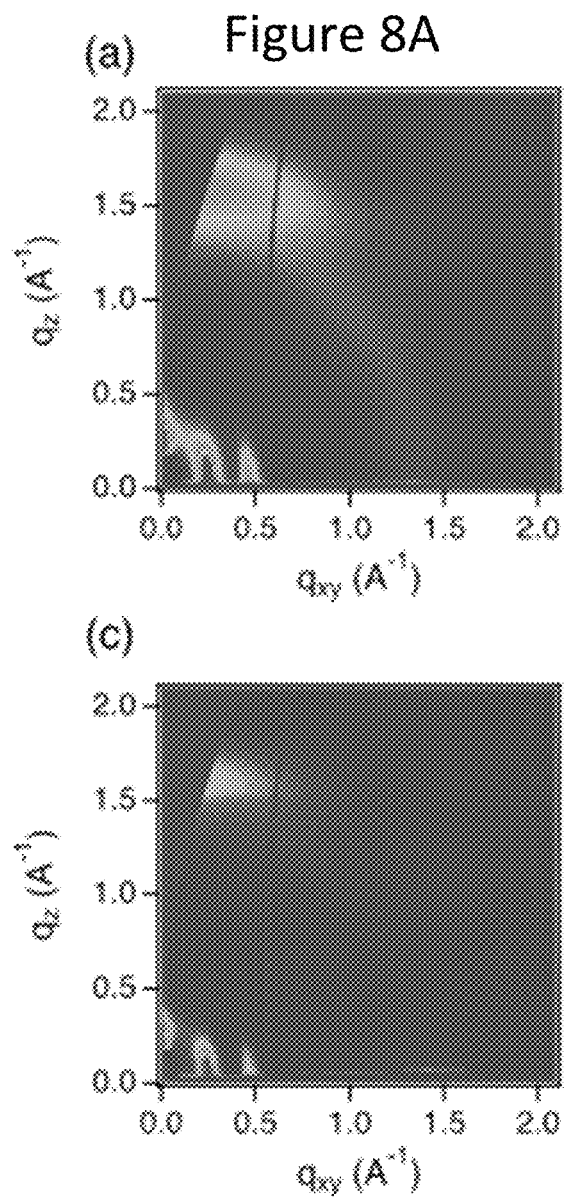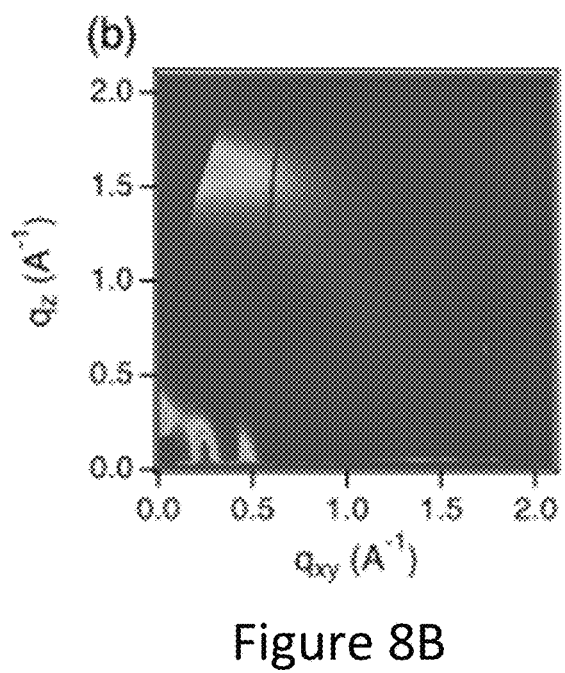
Figure 8A
Figure 8B
Figure 8C

NMR:

N-TYPE DOPANTS FOR EFFICIENT SOLAR CELLS

CROSS REFERENCE TO RELATED APPLICATIONS

This application is a divisional application under 35 U.S.C Section 121 of and commonly assigned U.S. Utility application Ser. No. 16/712,206, filed Dec. 12, 2019, by Julia Schneider, Michael L. Chabinyc, Hengbin Wang, Hidenori Nakayama, Kyle D. Clark, and Javier Read de Alaniz, entitled "N-TYPE DOPANTS FOR EFFICIENT SOLAR CELLS," which application claims the benefit under 35 U.S.C. Section 119(e) of commonly-assigned U.S. Provisional Patent Application No. 62/778,865, filed Dec. 12, 2018, by Julia Schneider, Michael L. Chabinyc, Hengbin Wang, Hidenori Nakayama, Kyle D. Clark, and Javier Read de Alaniz, entitled "N-TYPE DOPANTS FOR EFFICIENT SOLAR CELLS,";

all which applications are incorporated by reference herein.

BACKGROUND OF THE INVENTION

1. Field of the Invention

The present invention relates to n-type dopants for organic devices.

2. Description of the Related Art (Note: This application references a number of different publications as indicated throughout the specification by one or more reference numbers as superscripts, e.g., [x]. A list of these different publications ordered according to these reference numbers can be found below in the section entitled "References." Each of these publications is incorporated by reference herein.)

Chemical doping of organic semiconductors is necessary to increase conductivity and decrease carrier-injection barriers by shifting Fermi levels and filling trap states.[1] As the use of organic semiconductors (OSC) in such applications as solar cells, light-emitting diodes, field-effect transistors, and thermoelectric devices increases, so too does the need for efficient chemical dopants. Particularly sought after are n-type dopants with low ionization potentials that remain air-stable. N-dopants with low ionization potentials—tetrathiafulvalene TTF is a prevalent example—are not stable under ambient conditions due to low oxidation potentials.[2] circumvent this issue, past strategies have included generating the reductive species in-situ from a stable precursor, for example the hydride-donor leuco crystal violet (LCV) from the crystal violet salt[3] or benzimidazoline radicals from the corresponding dimer, (2-Cyc-DMBI)$_2$.[4] In these cases, however, the resulting reduced byproduct must be innocuous to device performance.

SUMMARY OF THE INVENTION

The present disclosure reports on a composition of matter useful as a n-type dopant for organic devices. The composition of matter can be embodied in many ways including, but not limited to, the following.

1. A composition of matter including an organic compound of the structure:

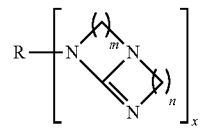

wherein:

1≤M≤8;

1≤n≤8;

2≤x≤4; and

R is any substituted or non-substituted alkyl, alkenyl, alkynyl, aryl or alkoxy group.

2. The composition of matter of embodiment 1, wherein R contains one or more heteroatoms.

3. The composition of matter of embodiments 1 or 2, wherein R contains one or more aromatic moieties.

4. The composition of matter of any of the preceding embodiments, wherein

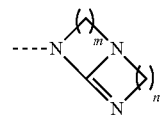

is any of the following bicyclic structures:

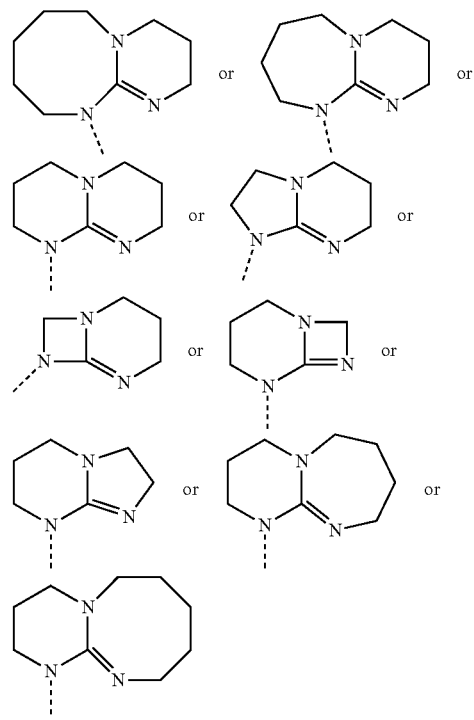

The composition of matter of any of the preceding embodiments, wherein the organic compound is a dirtier (x=2) wherein each end of the R is connected to one of the

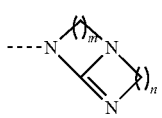

6. The composition of matter of embodiment 5, wherein the organic compound is

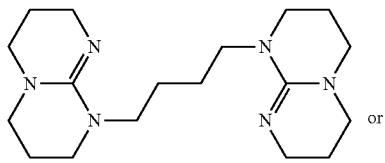

2TBD-C$_4$

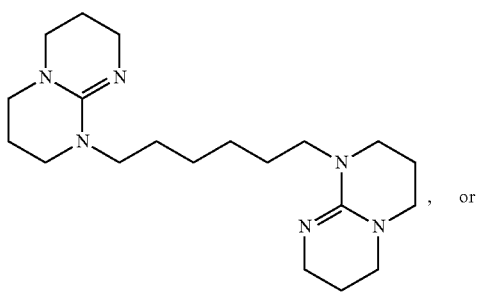

, or

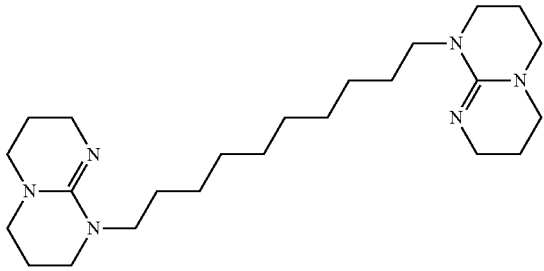

7. The composition of matter of any of the embodiments 1-4, wherein the organic compound is a trimer (x=3) wherein each end of the R is connected to one of the

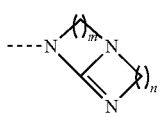

The composition of matter of embodiment 7, wherein the organic compound is

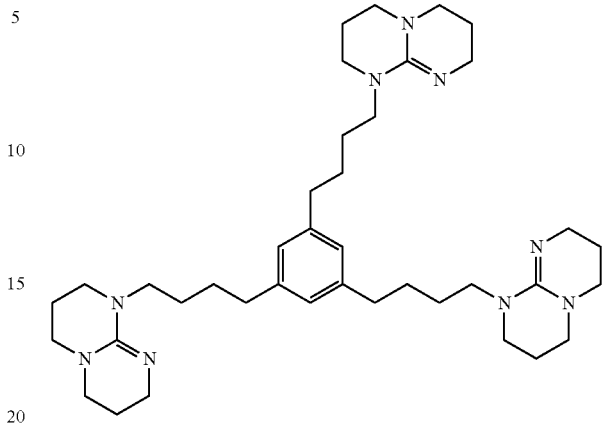

9. The composition of matter of any of the preceding embodiments bonded to a fullerene, or wherein the R comprises a fullerene, so as to n-type dope the fullerene.

10. The composition of matter of any of the preceding embodiments 1-8 bonded to a phenyl-C$_{61}$-butyric acid methyl ester (PCBM) or Poly{[N,N'-bis(2-octyldodecyl-napthalene-1,4,5,8-bis(dicarboximide)-2,6-diyl]-alt-5,5'-(2,2'-bithiophene)}(N2200) so as to n-type dope the PCBM or the N2200.11. The composition of matter of any of the preceding embodiments 1-8 bonded to an electron acceptor (e.g., comprising a second organic compound) so as to n-type dope the acceptor.

12. The composition of embodiment 1 bonded to a fullerene so as to form the compound

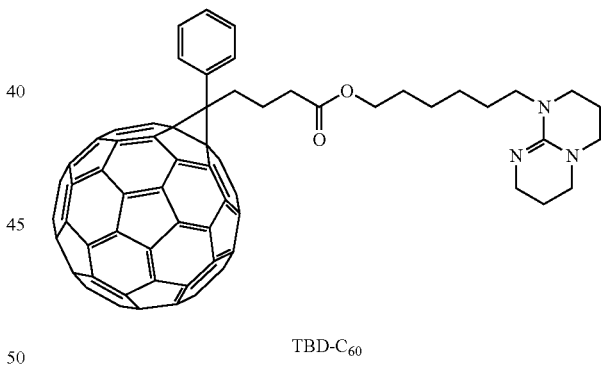

TBD-C$_{60}$

13. The composition of matter of any of the preceding embodiments, wherein the R is selected so that the organic compound is miscible with an organic acceptor (e.g., comprising a second organic compound).

14. The composition of matter of embodiment 13, further comprising a single phase amorphous composition including the organic compound combined with the organic acceptor, wherein the organic compound n-type dopes the organic acceptor.

15. A device comprising the organic compounds of any of the preceding embodiments, wherein the device is a light emitting device, a light absorbing device, a thermoelectric device, or a transistor.

16. The device of embodiment 15, further comprising an active region or electron transporting layer including the organic compound.

17. The device of embodiment 16, wherein the organic compound is n-type self-doped such that the organic compound emits light in response to current, transports current in a channel of a transistor, or generates current in response to light.

18. The device of embodiment 16, wherein the active region or the electron transporting layer includes an organic acceptor combined with the organic compound so that the organic compound n-type dopes the organic acceptor.

19. The device of embodiments 15-18, wherein the organic compound is non-volatile and stable in air up to a temperature of at least 200 degrees Celsius.

20. A device, comprising:
an organic transistor, an organic light absorbing device, a hybrid solar cell device, a photodetector device, a thermoelectric device, or an organic light emitting device comprising an n-type dopant including an organic compound of the structure:

$$R \left[ N \left( \underset{N}{\overset{N}{\bigwedge}}_{m} N \right)_n \right]_x$$

wherein:
$0 \leq m \leq 8$;
$0 \leq n \leq 8$;
$1 \leq x \leq 4$;
and R is any substituted or non-substituted alkyl, alkenyl, alkynyl, aryl or alkoxy group.

21. The device of embodiment 20, wherein R contains one or more heteroatoms.

22. The device of embodiments 20 or 21, wherein R contains one or more aromatic moieties.

23. The device of any of the embodiments 20-22, further comprising a light emitting active region including the n-type dopant.

24. The device of any of the embodiments 20-22 further comprising a light absorbing active region including the n-type dopant.

25. The device of any of the embodiments 20-22, wherein the device is a transistor further comprising a conductive channel including the n-type dopant.

Examples of composition and device fabricated and characterized herein include, but are not limited to, a series of novel 1,5,7-Triazabicyclo[4.4.0]dec-5-ene (TBD) derivatives as air-stable n-dopants for organic semiconductors. These compounds have a guanidine structure which works as an electron-dopant and a long alkyl chain at the 7-position which increases their boiling point and solubility. This structural feature makes the compounds highly efficient and non-volatile n-dopants. Adding these compounds in the electron transport layer (ETL) of methylammonium lead iodide based solar cells increases the conductivity of the ETL and the solar cell efficiency.

BRIEF DESCRIPTION OF THE DRAWINGS

Referring now to the drawings in which like reference numbers represent corresponding parts throughout:

FIG. 3A and FIG. 3B show cyclic voltammetry of C10-TBD and 2TBD-C10, wherein FIG. 3A shows potential (V) vs. Fc/Fc$^+$ and FIG. 3B shows potential (V) vs. Ag/Ag$^+$.

FIGS. 8A-8C. 2-Dimensional GIWAXS images of pristine N2200 (FIG. 8A), N2200 with 10 mol % 2TBD-C10 (FIG. 8B), and 12200 with 10 mol % TBD-C10 (FIG. 8C).

Figure 12A:
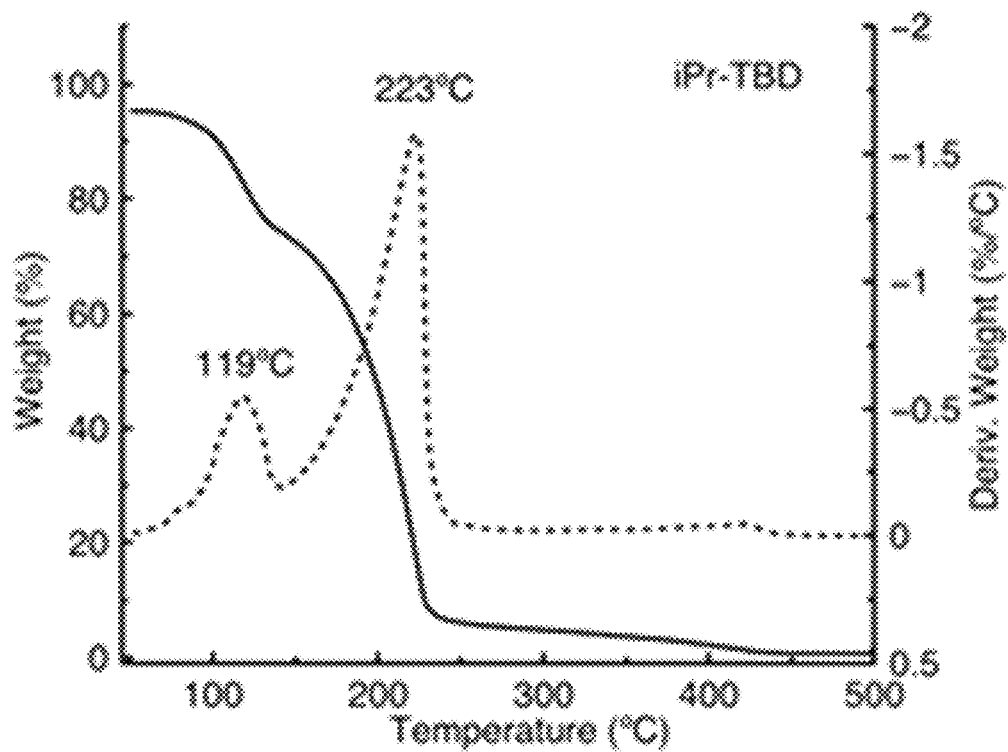
FIGS. 12A-12E. TGA and first derivative curves of the dopants under nitrogen flow, for the dopant iPR-TBD (FIG.
Figure 12B:
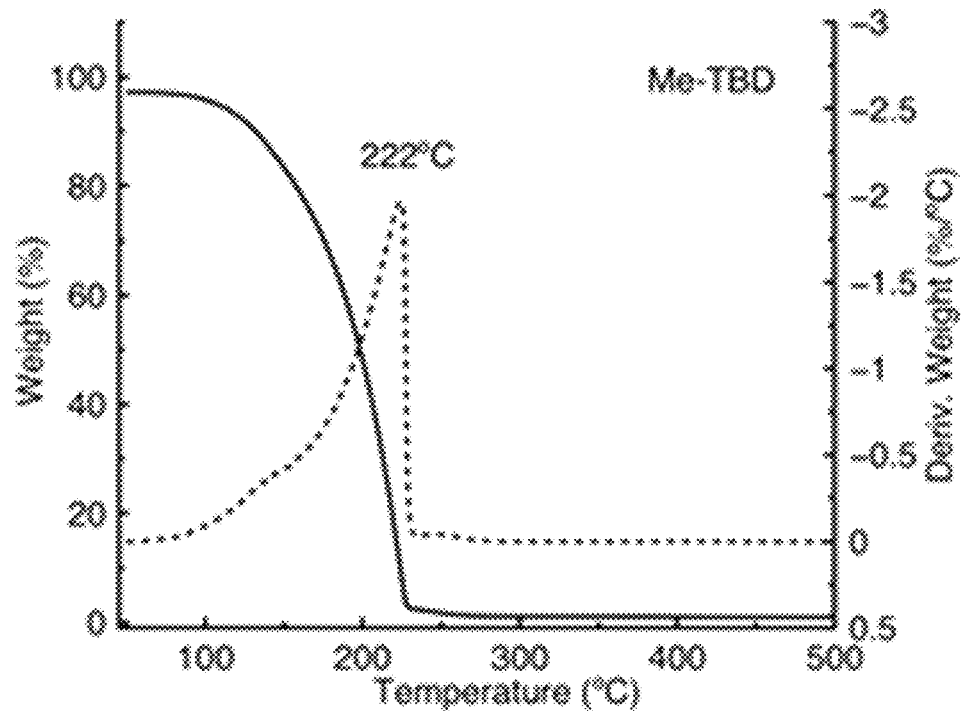
Figure 12C:
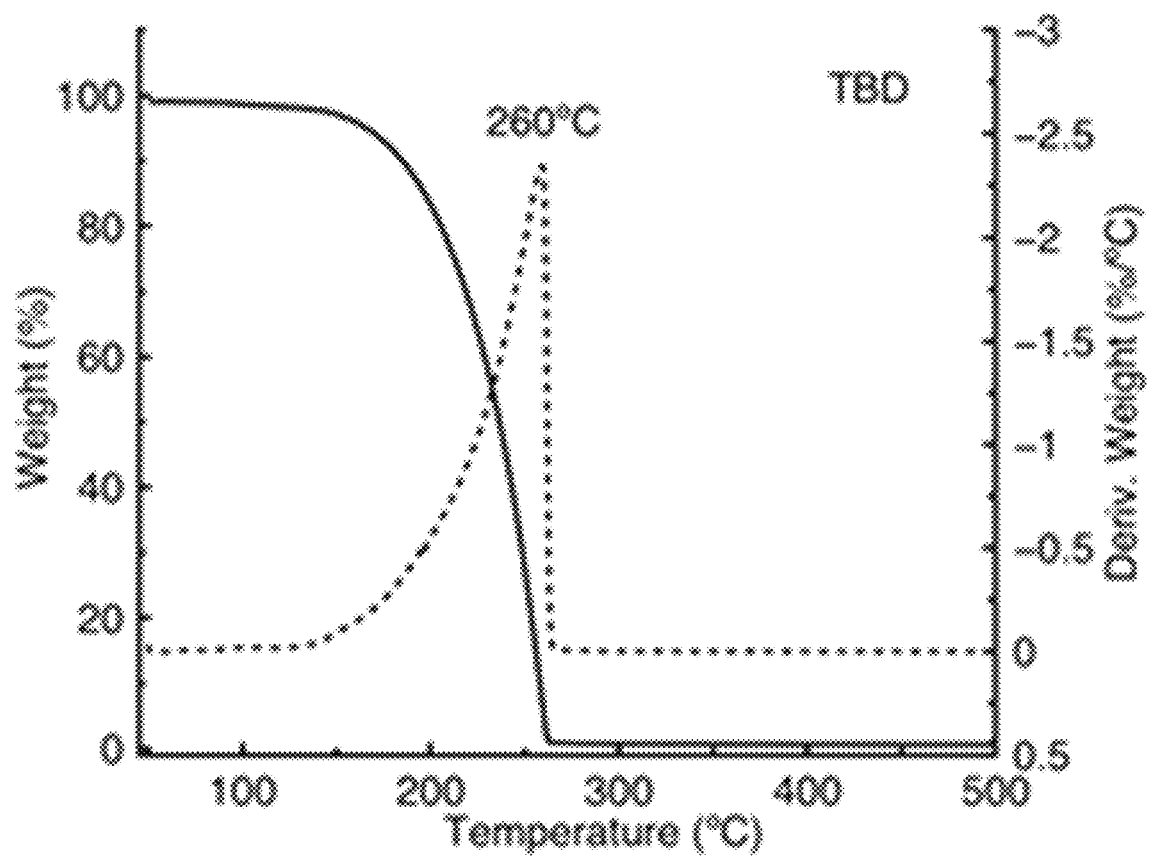
Figure 12D:
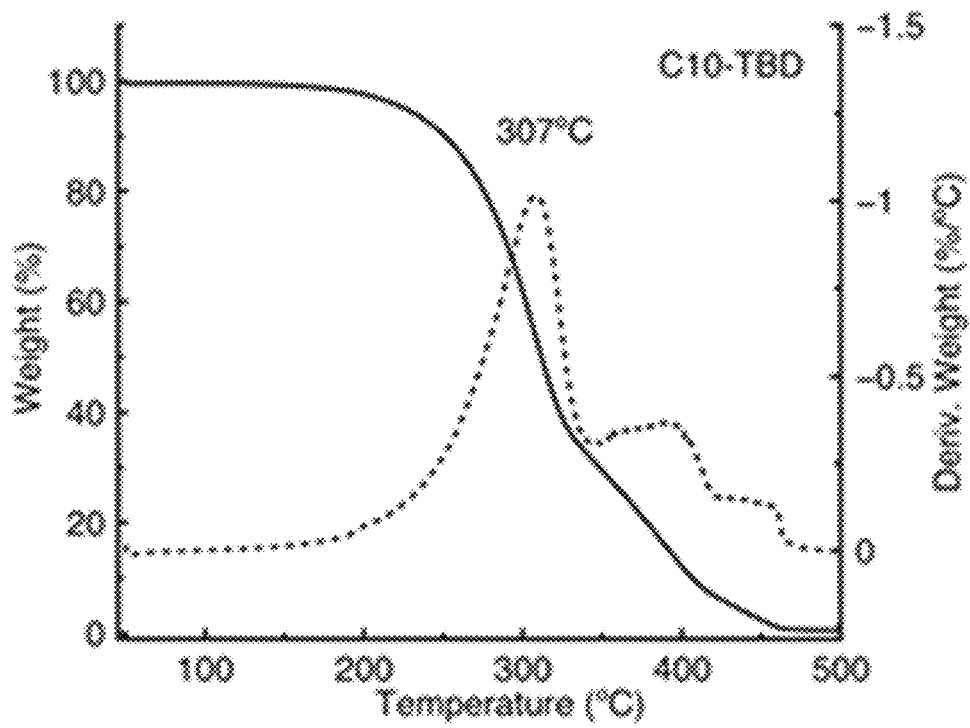
Figure 12E:
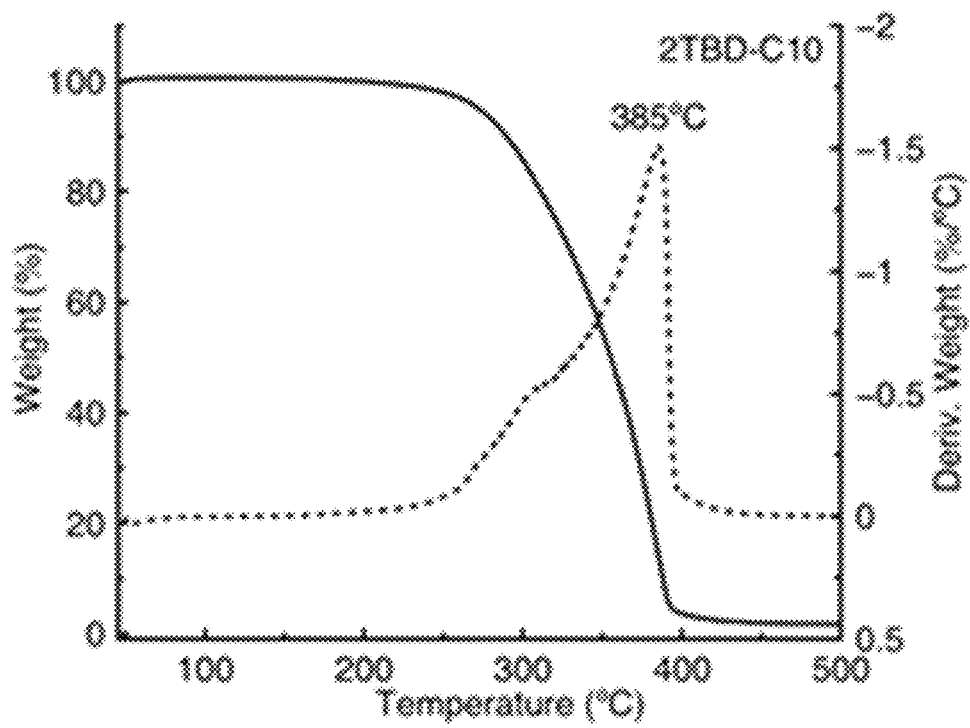

12A), Me-TBD (FIG. 12B), TBD (FIG. 12C), C$_{10}$-TBD (FIG. 12D), and 2TBD-C$_{10}$ (FIG. 12E).

Figure 13A:
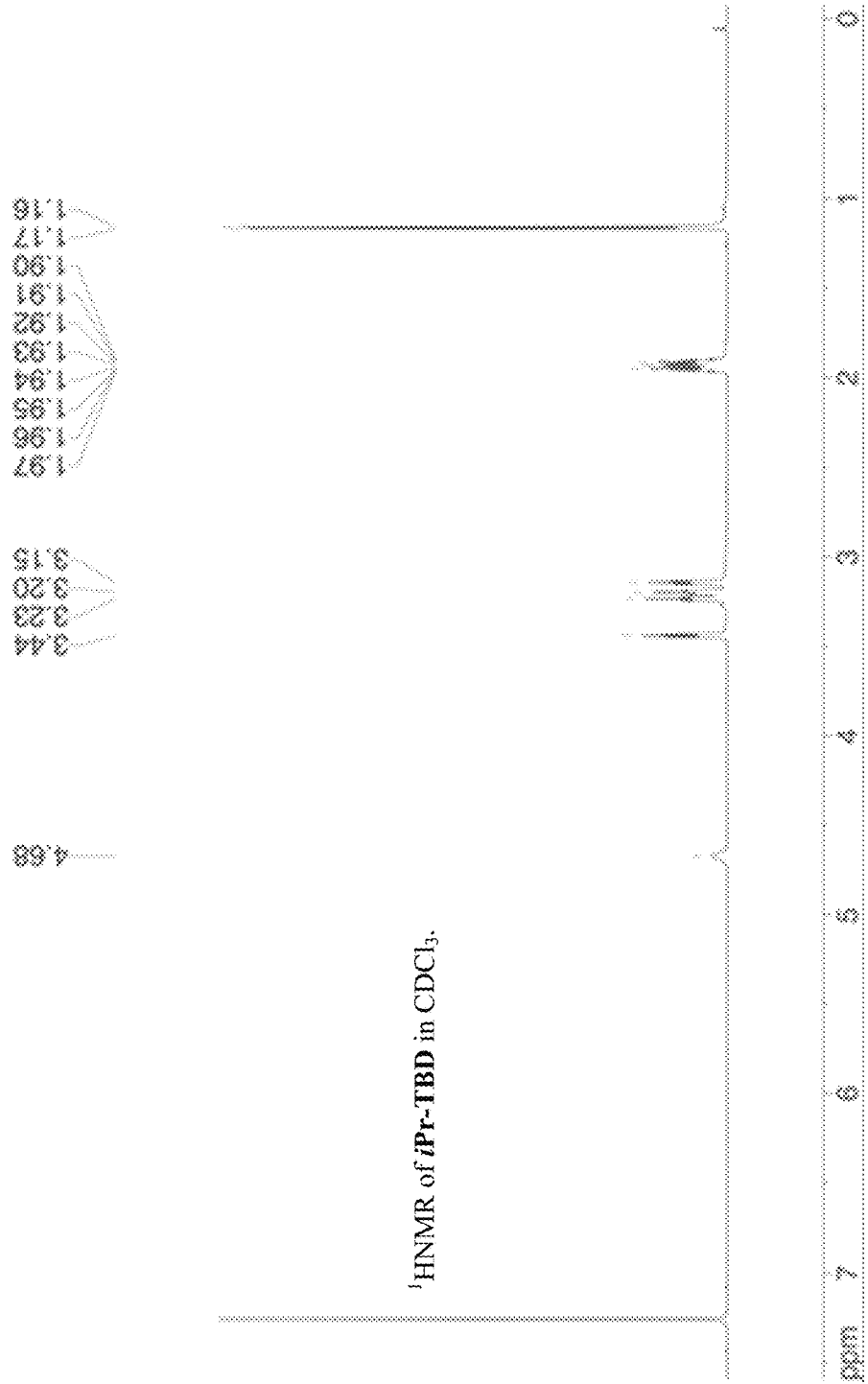
Figure 13B:
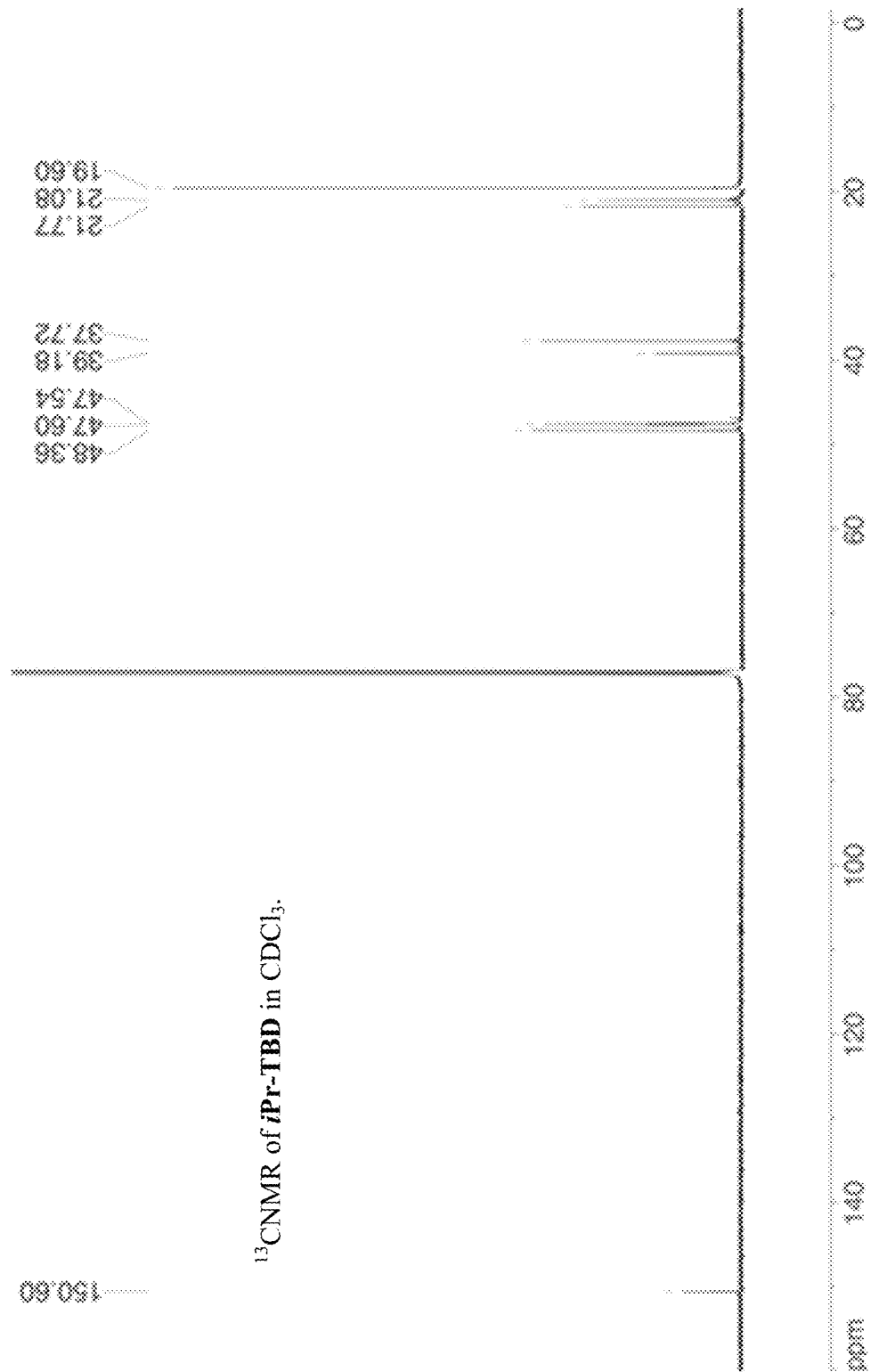
Figure 13C:
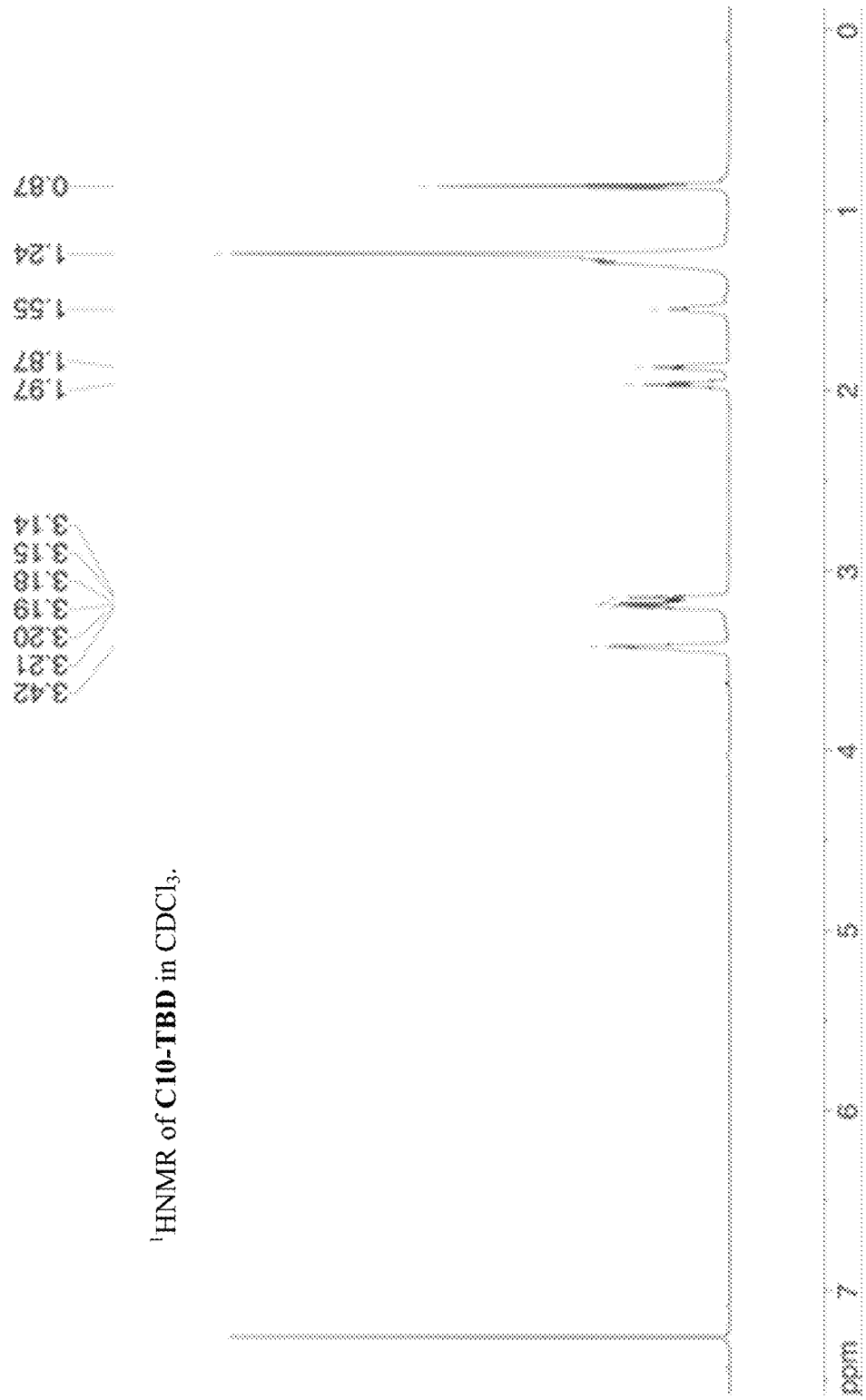
Figure 13D:
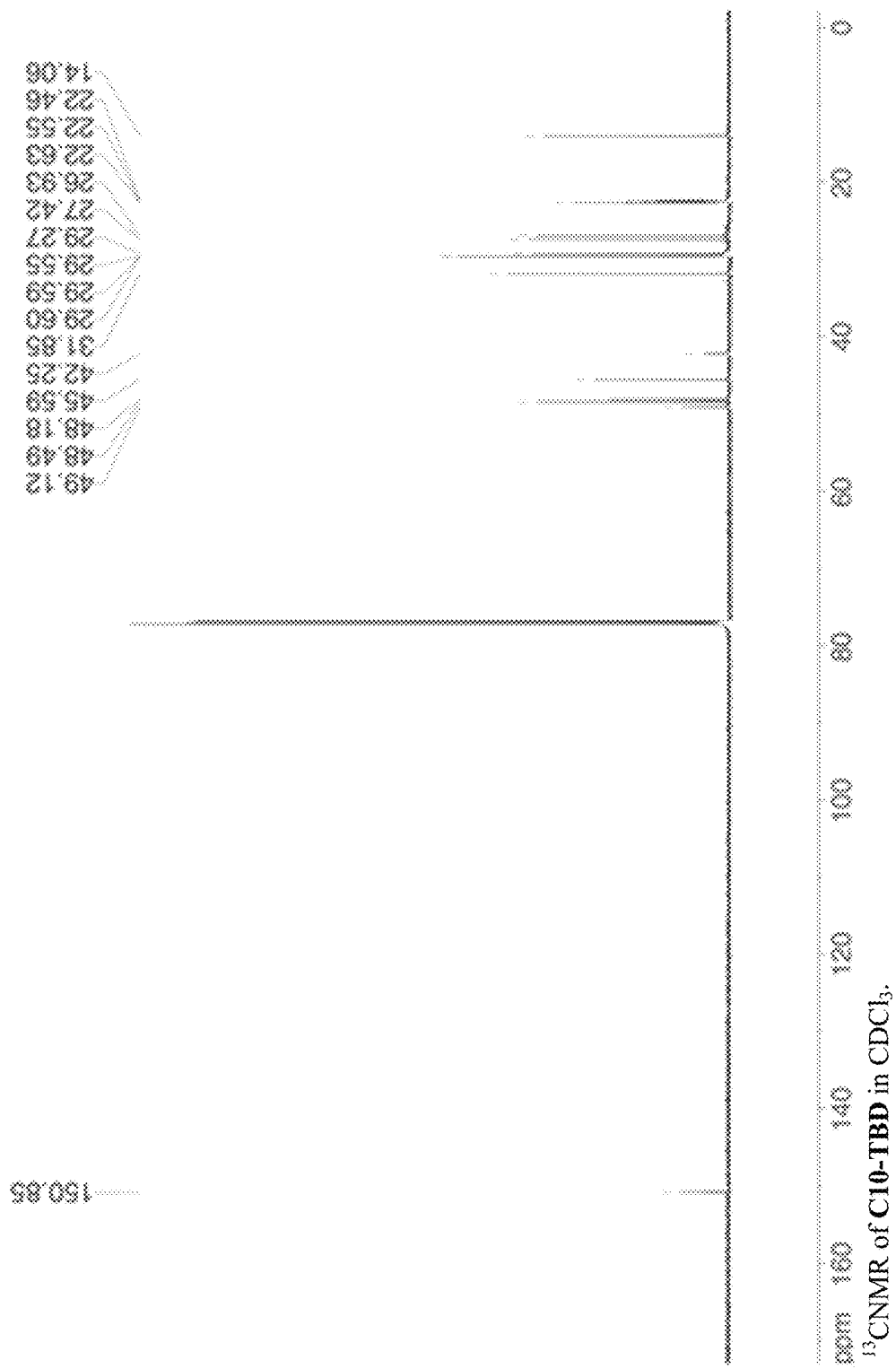
Figure 13E:
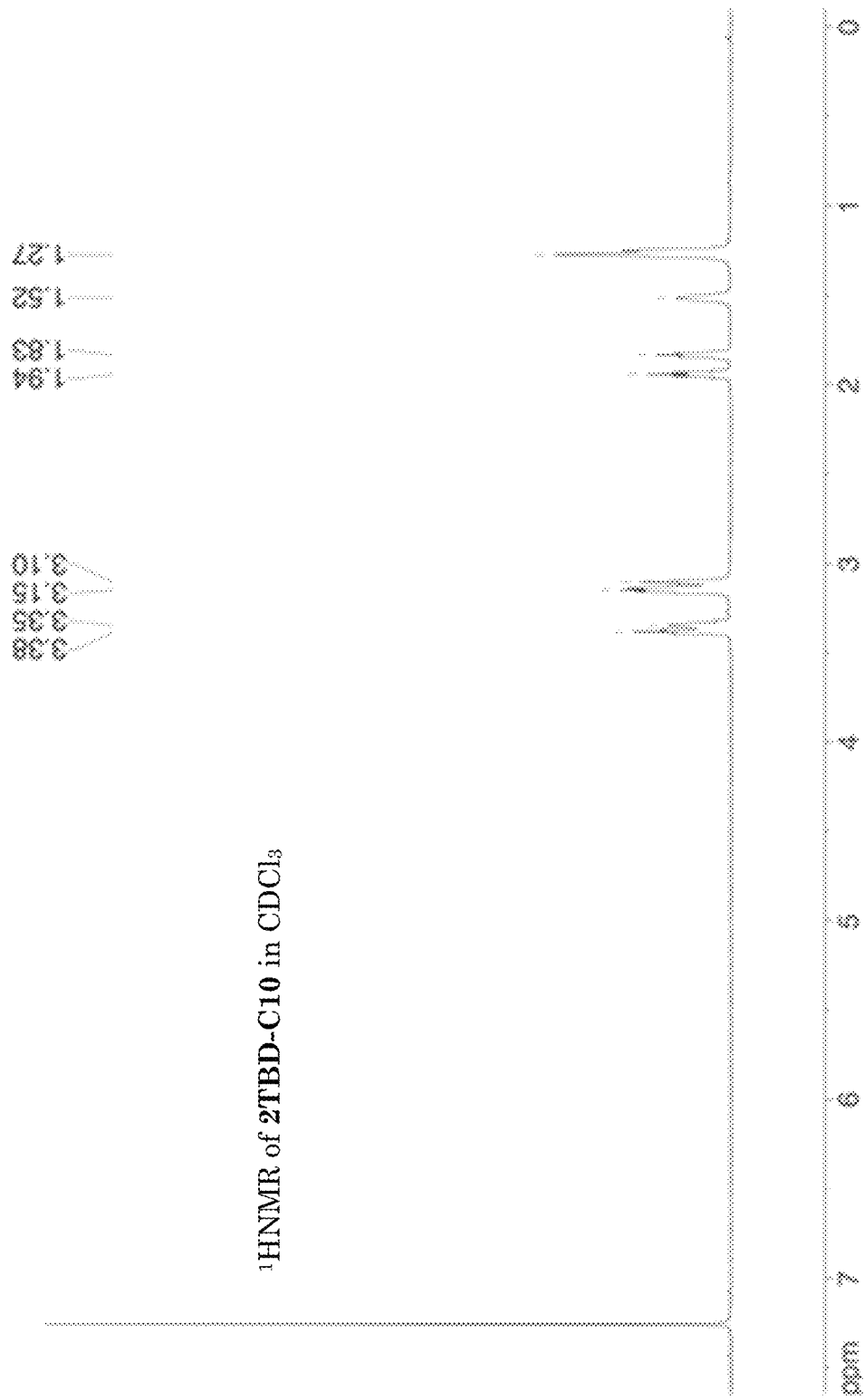
Figure 13F:
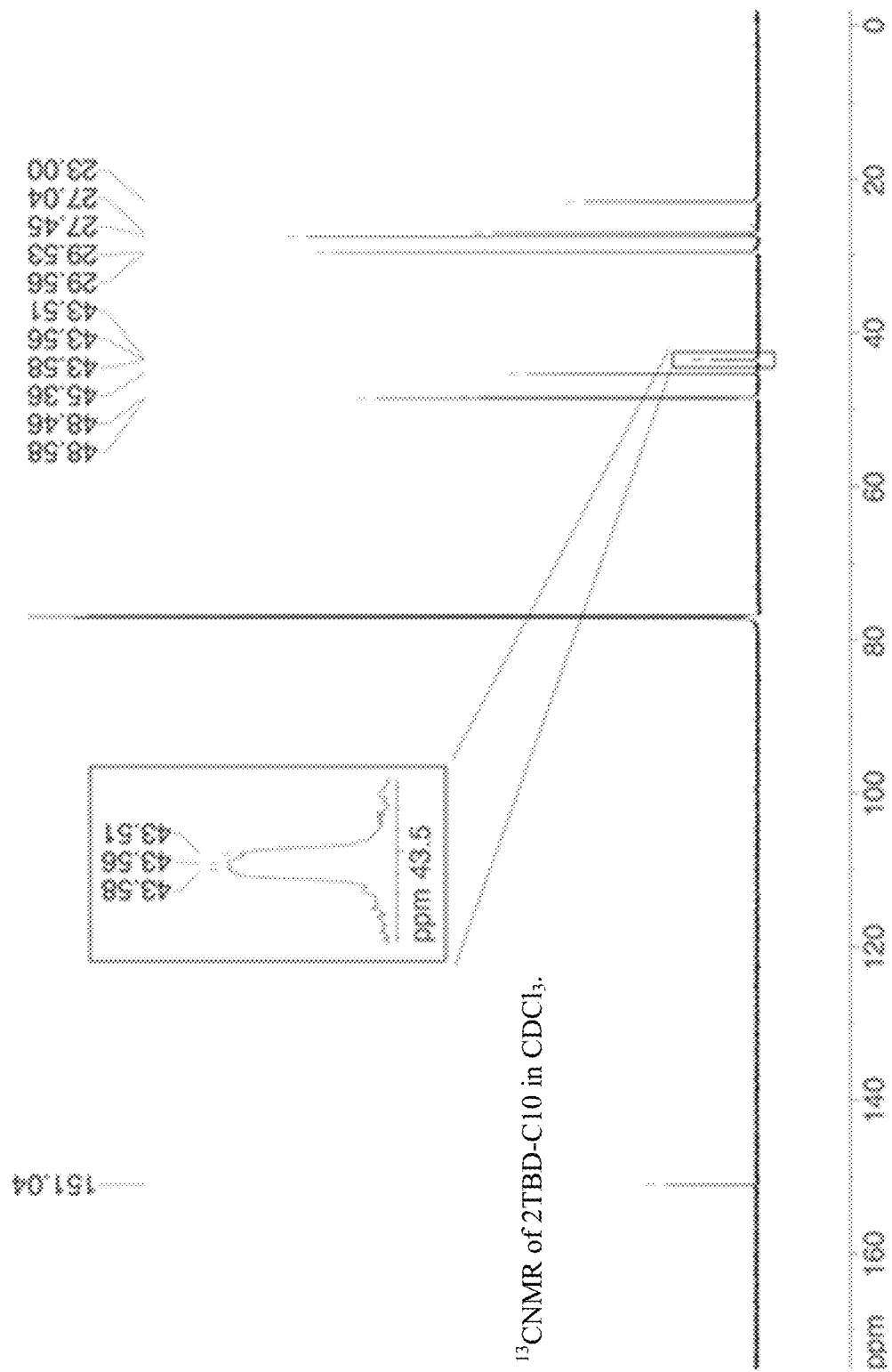

FIGS. 13A-13F. Nuclear Magnetic Resonance (NMR) measurements of various triazabicyclodecene-based compounds including NMR of iPr-TBD in CDCl$_3$ (FIG. 13A, $^1$H NMR; FIG. 13B, $^{13}$C NMR), C$_{10}$-TBD in CDCl$_3$ (FIG. 13C, $^1$H NMR; FIG. 13D; $^{13}$C NMR), 2TBD-C10 in CDCl$_3$ (FIG. 13E, $^1$H NMR; FIG. 13F. $^{13}$C NMR)

Figure 14:
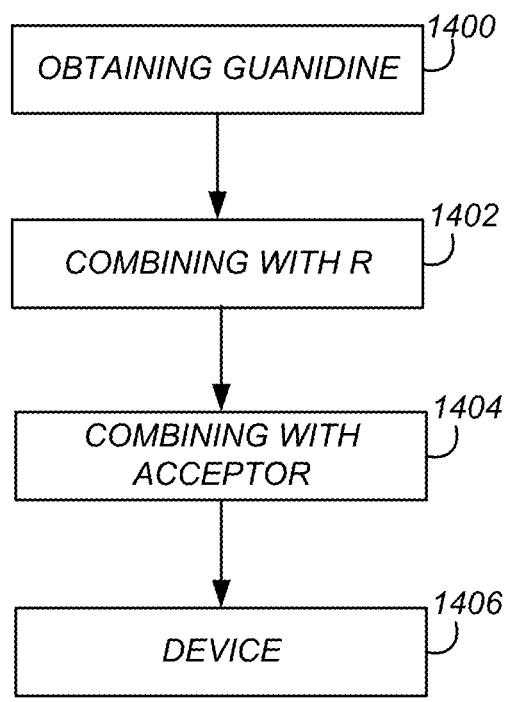

FIG. 14. Flowchart illustrating a method of making an n-type dopant and/or device including the n-type dopant.

Figure 15:
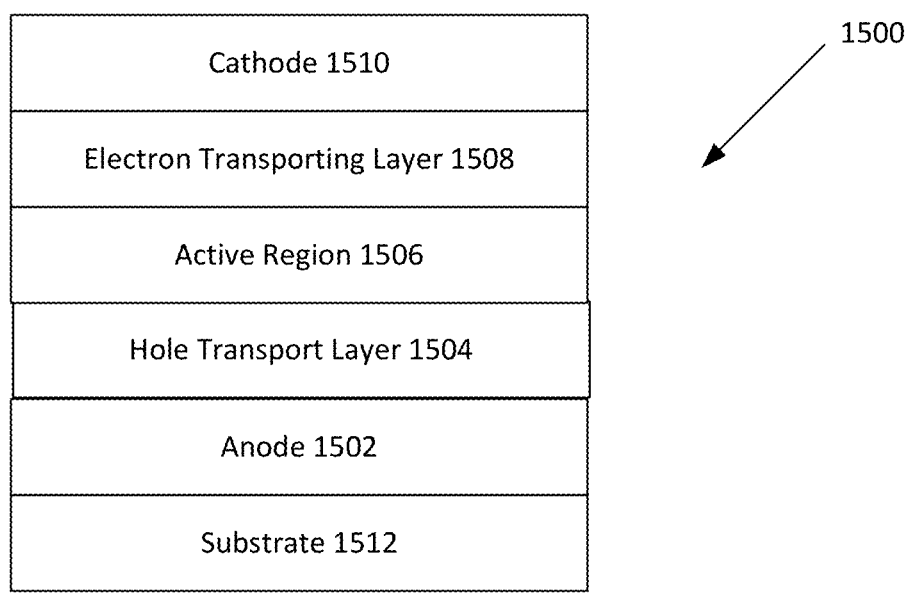

FIG. 15 illustrates a solar cell or photodetector including an organic compound according to one or more embodiments described herein.

Figure 16:
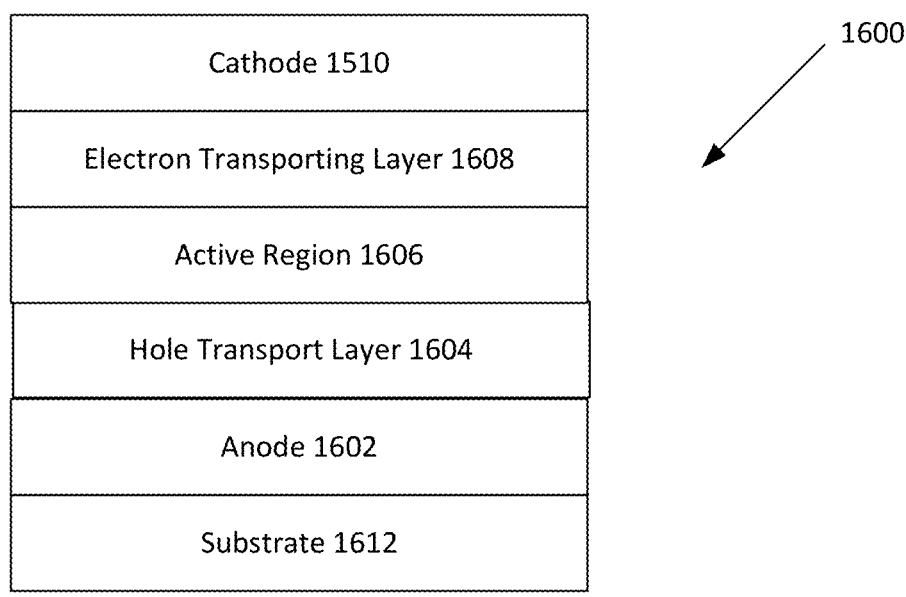

FIG. 16 illustrates an organic light emitting diode (OLED) including an organic compound according to one or more embodiments described herein.

Figure 17:
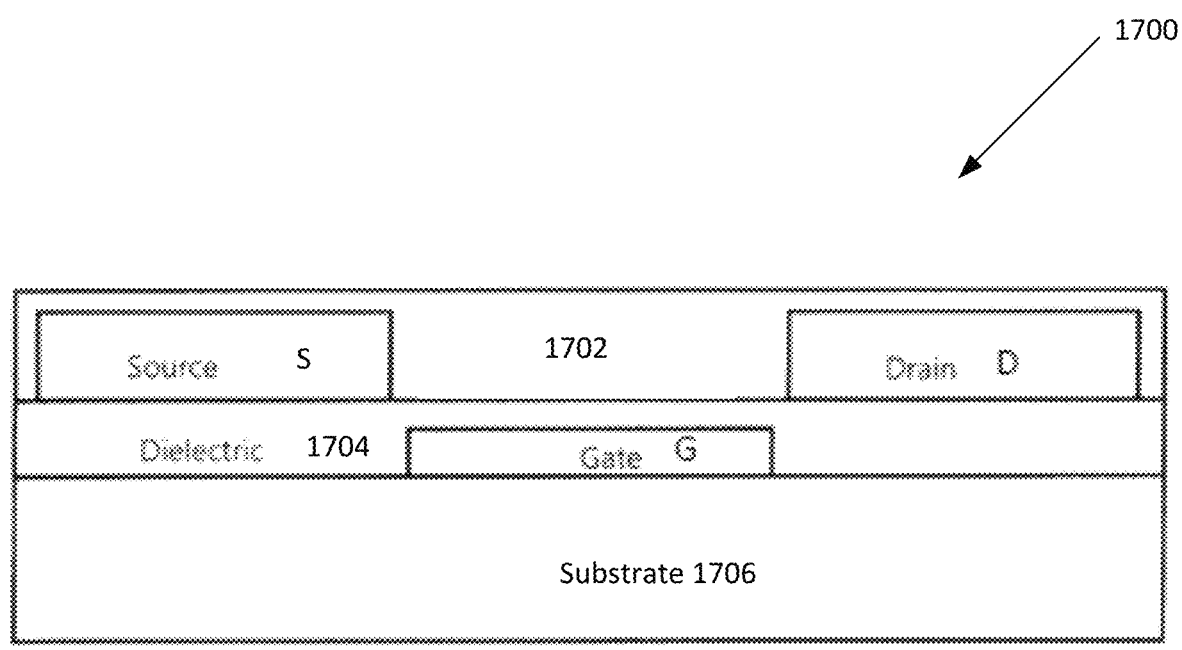

FIG. 17 illustrates an organic field effect transistor including an organic compound according to one or more embodiments described herein.

Figure 18:
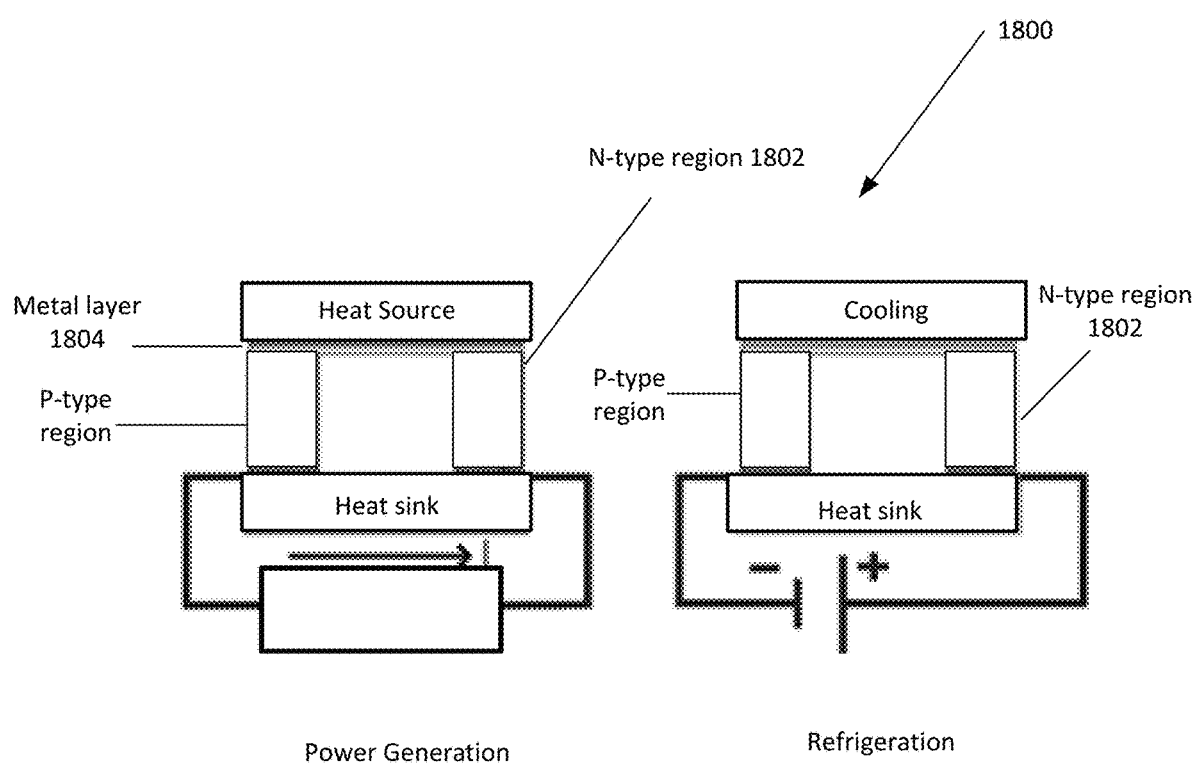

FIG. 18 illustrates a thermoelectric device including an organic compound according to one or more embodiments described herein.

Figure 19:
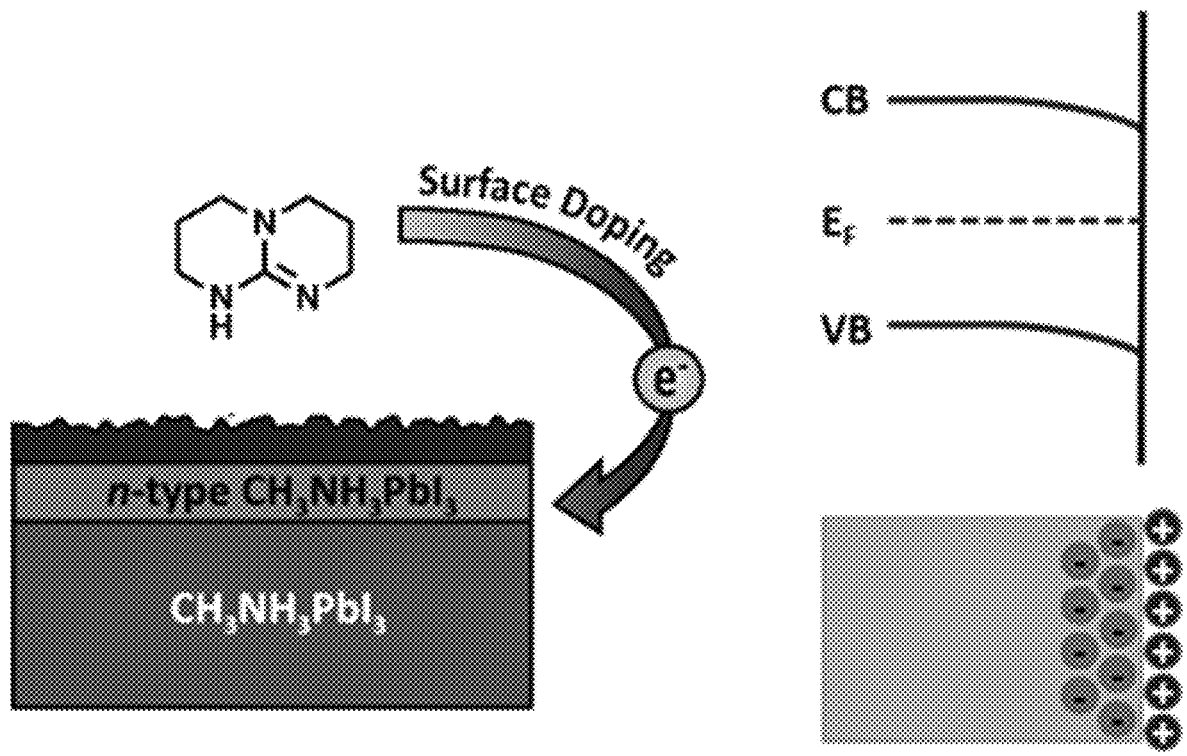

FIG. 19. Schematic illustrating the operation of the n-type dopant.

DETAILED DESCRIPTION OF THE INVENTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

A. Example Compositions

Figure 1:
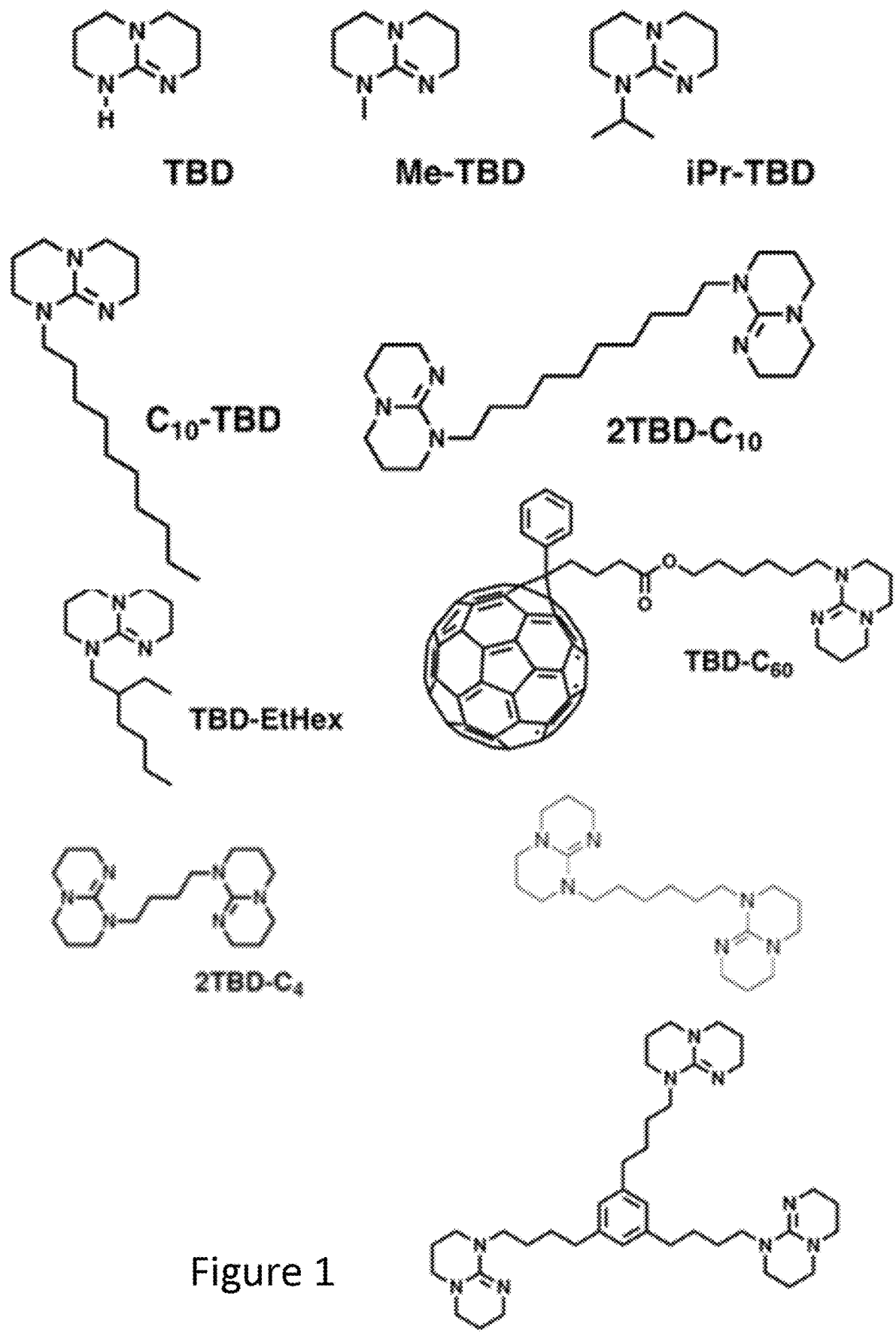
FIG. 1 illustrates chemical structures of example n-type dopants based on triazabicyclodecene.

FIG. 1 illustrates a series of triazabicyclodecene-based compounds used as n-dopants with varying physical properties, namely TBD, iPr-TBD, Me-TBD, C10-TBD, 2TBD-C10. Introducing a variety of N-substituents enabled control of the volatility of the materials and whether they were solid or liquid. For example, doubling the ratio of TBD groups to alkyl chain in 2TBD-C10 gave a solid material with high thermal stability above 250° C. All the TBD n-dopants effectively increase the conductivity of PCBM films, with 2TBD-C10 achieving a high of 6.5×10$^{-2}$ Siemens per centimeter (S/cm). 2TBD-C10 was also shown to effectively dope poly{[N,N'-bis(2-octvidodecyl)naphthalene-1,4,5,8-bis(dicarboximide)-2,6-diyl]-alt-5,5'-(2,2'-bithiophene)} (P(NDI2OD-T2), also called N2200) and 3,9-bis(2-methylene-(3-(1,1-dicyanomethylene)-indanone))-5,5,11,11-tetrakis(4-hexylphenyl)-dithieno[2,3-d:2',3'-d']-s-indaceno[1,2-b:5,6-b']dithiophene (ITIC). In perovskite solar cells the use of PCBM doped by 2TBD-C10 led to improved fill factors and PCEs.

The guanidine-type dopants described herein are effective electron donors due to the three nitrogen atoms that stabilize the central carbocation. The following sections report on the effectiveness of these TBD molecules as n-dopants, the effect substituents have on the physical properties, thermal stability, and resulting performance of these materials.

a. Example General Synthetic Procedure of TBD Dopants 1,5,7-Triazabicyclo[4.4.0]dec-5-ene (TBD) and 7-methyl-1,5,7-triazabicyclo[4.4.0]dec-5-ene (Me-TBD) were commercially available and used without further purification. TBD was readily alkylated by deprotonating with sodium hydride and quenching with alley bromide to yield iPr-TBD, C10-TBD, and 2TBD-C10. While TBD is a crystalline white solid, Me-TBD, iPr-TBD, and C10-TBD are oils, iPr-TBD being by far the most viscous. 2TBD-C10, on the other hand, with double the TBD moiety ratio to alkyl chain, is a white powdery solid. All the dopants are readily soluble in both polar and non-polar organic solvents, as well as water and methanol. This allows for versatile processing, employing either blends or sequential applications with anti-solvents.

The general synthetic procedure for TBD dopants and derivatives characterized herein is as follows.

First TBD was reacted with excess amount of sodium hydride at room temperature for two hours, then alkyl bromide was added to further react for 12-24 hours at room temperature to achieve the TBD dopants.

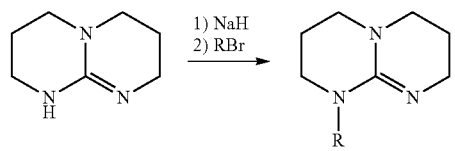

The advantages of this synthetic method and products include one pot synthesis, air stable products, and control volatility/greasiness with the choice of alkyl group. Moreover, the product can be both water and organic soluble which allows for blend or sequential processing in device fabrication.

The synthesis of 2TBD-C$_{10}$ was as follows.

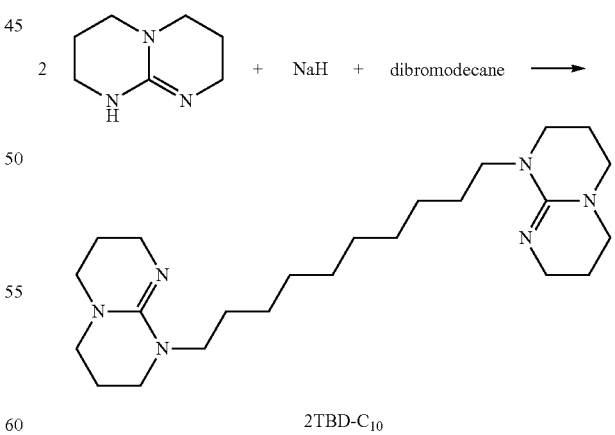

2TBD-C$_{10}$

Solid

Water soluble

Organic soluble

The synthesis of TBD-C$_{60}$ is as follows.

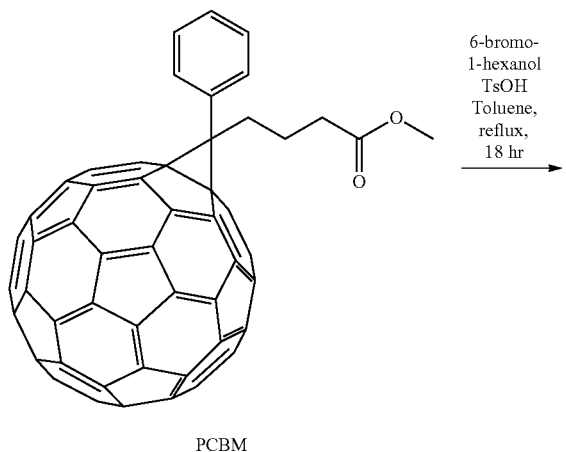
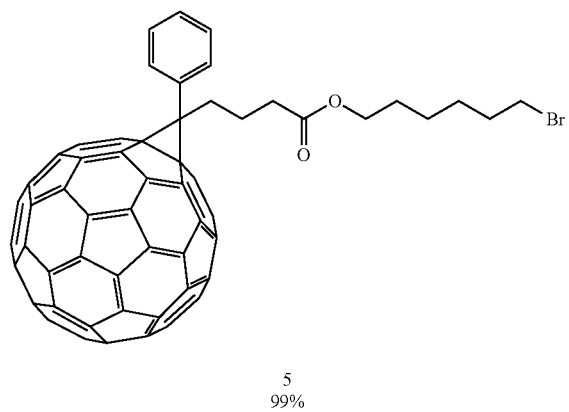
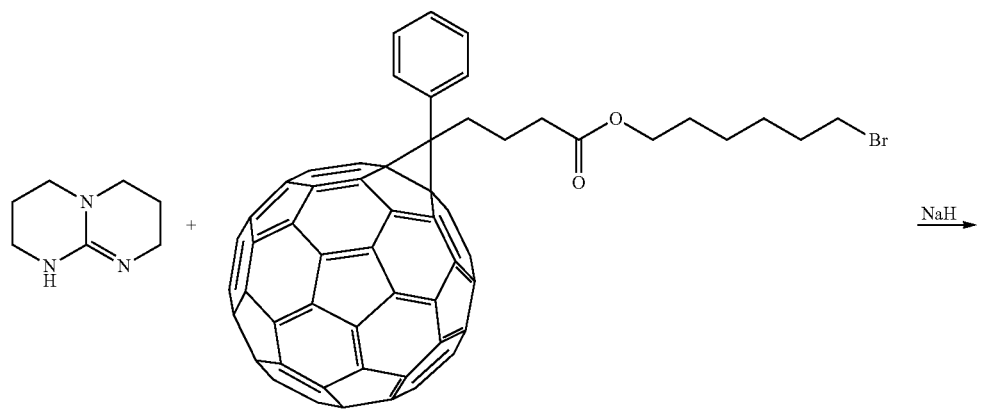

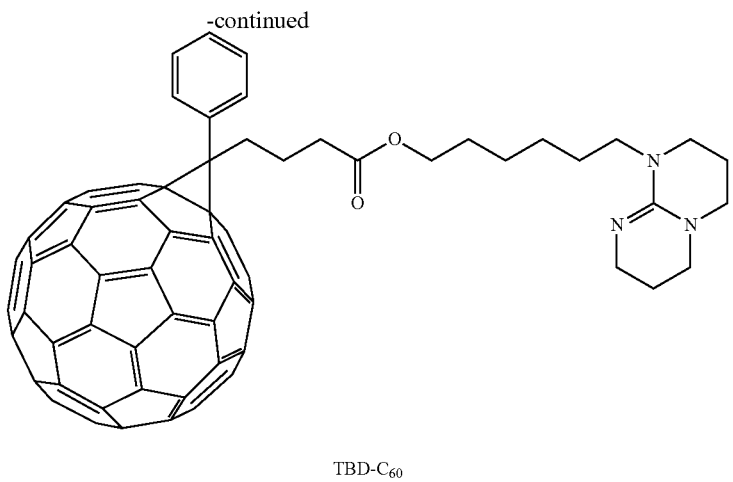

TBD-C$_{60}$

TBD-C$_{60}$ dyad was synthesized in two steps following the scheme above. Covalently attaching TBD to PCBM can reduce the phase separation of the TBD when the TBD is blended with the fullerene-based acceptors. Surprisingly, the product is very insoluble in various solvents, which indicates that the TBD may be already self-doped at room temperature with the TBD unit as the electron donor and the fullerene cage as the electron acceptor (due to the close proximity of the two units).

The synthesis of TBD-Cylic-C4 was as follows.

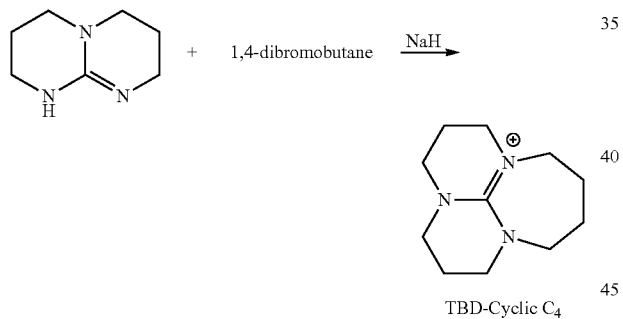

TBD-Cyclic C$_4$

When 1,4-dibromobutane was used, instead of 2TBD-C4, a charged tricyclic product TBD-Cylic-C4 was achieved as shown above, which was tested as a n-type dopant too. 2TBD-C4 can be synthesized using a different pathway.

b. Thermal Stability

Figure 2:
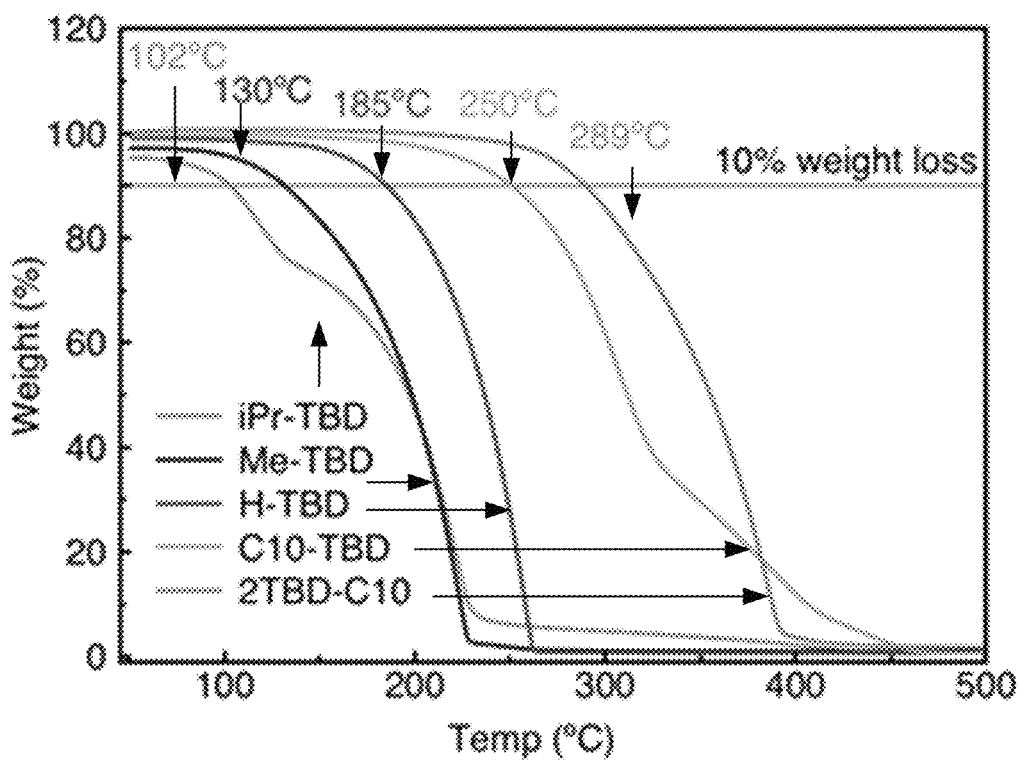
FIG. 2. Thermal Gravimetric Analysis (TGA) thermal curves for various dopants (iPr-TBD, Me-TBD, H-TBD (TBD), $C_{10}$-TBD, and 2TBD-$C_{10}$) under nitrogen. The temperature at which 10% weight loss is observed is listed above each curve.

A motivation behind modifying commercially available TBD was to enhance the stability of the dopant during processing since the volatility of a material could drastically alter the doping concentration in the device, especially after film coating and annealing. To this end, we quantified the thermal stability of our dopants through thermal gravimetric analysis (TGA) (FIG. 2). We found that modifying TBD with short alkyl chains, especially branched isopropyl, led to much lower initial decomposition (or evaporation, sublimation) temperatures. Longer alkyl chains like decyl, on the other hand, increased the thermal stability. 2TBD-C10, a solid like TBD, but with the added mass of the decyl chain, showed the highest thermal stability, with an initial decomposition temperature around 270° C.

c. Oxidation Potential

Figure 3A:
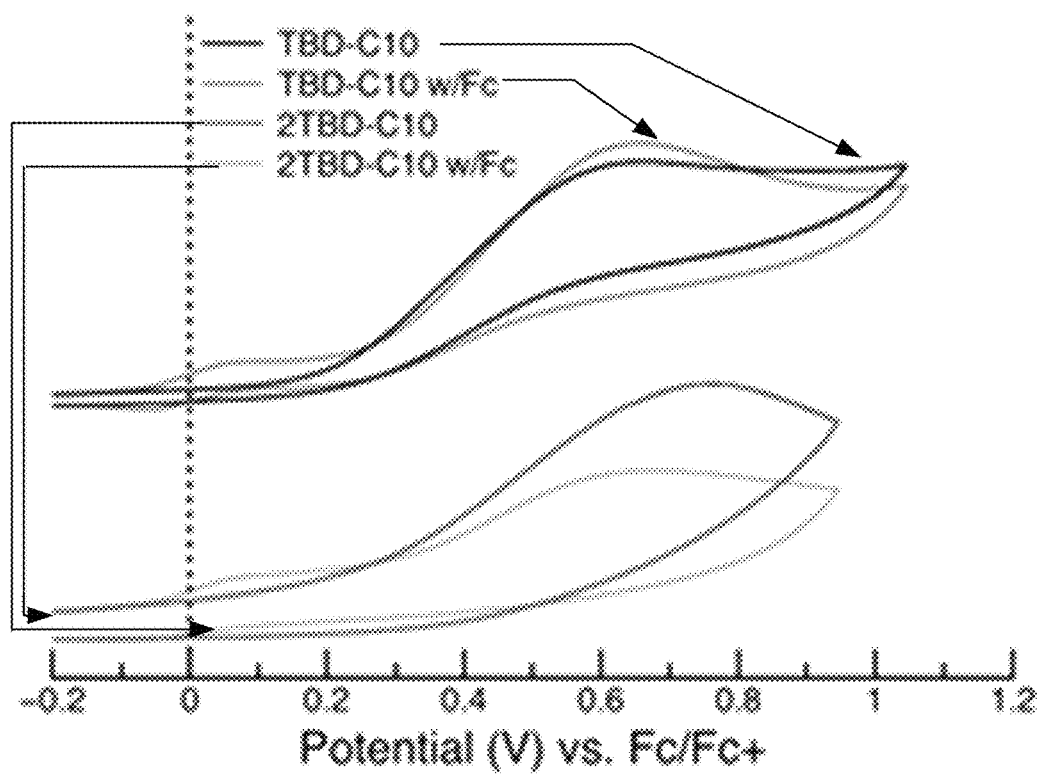
Figure 3B:
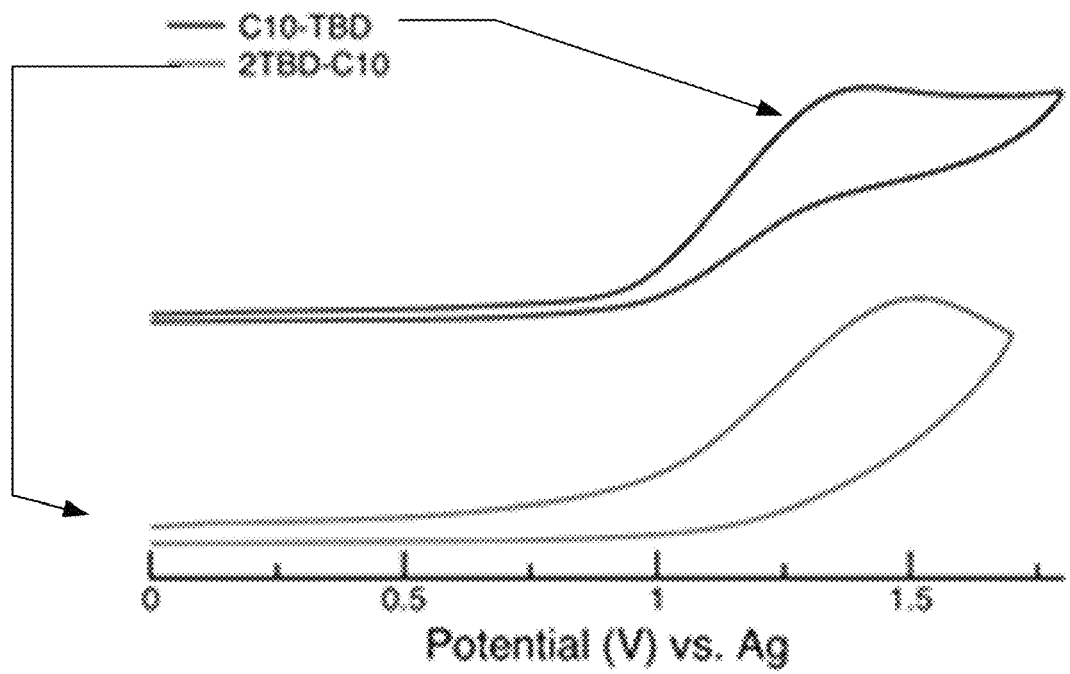

In order to act as efficient n-dopants, the TBD moiety must be readily oxidized. We used cyclic voltammetry to compare the oxidation potentials of C10-TBD and 2TBD-C10 (FIG. 3). Both dopants showed highly irreversible oxidation potentials, C10-TBD at 1.00 V and 2TBD-C10 at 1.05 V. This close match signifies that in 2TBD-C10, the two tethered TBD moieties are behaving independently. Versus a ferrocene internal standard, this represents Highest Unoccupied Molecular Orbital (HOMO) levels of about −5.1 eV for both dopants. The ability of these materials to n-dope PCBM with a Lowest Unoccupied Molecular Orbital (LUMO) level ca. −4.0 eV is indication of a stable, favored charged byproduct or the formation of an intermediate reducing species.

d. Conductivity

Figure 4:
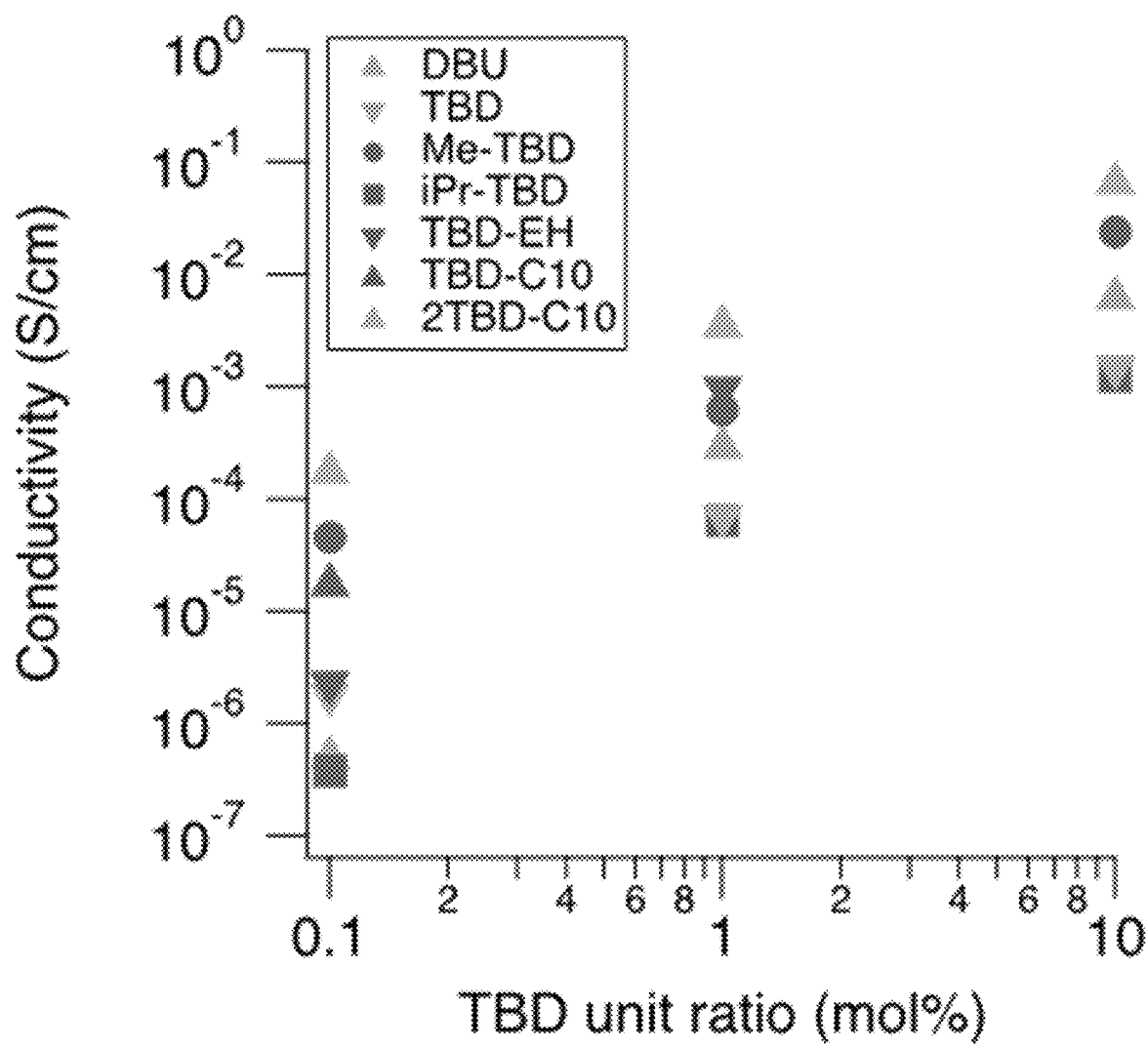
FIG. 4. Conductivities of doped PCBM films as a function of the molar ratio of TBD or DBU unit to PCBM. TBD-C10 has a data point only at 0.1 mol % since TBD-C10 doped PCBM solutions slipped off from quartz surface when the concentration was 1 or 10 mol %. TBD-EH data point at 10 mol % is also missing for the same reason.
Figures 5A, 5B, 5C, 5D:
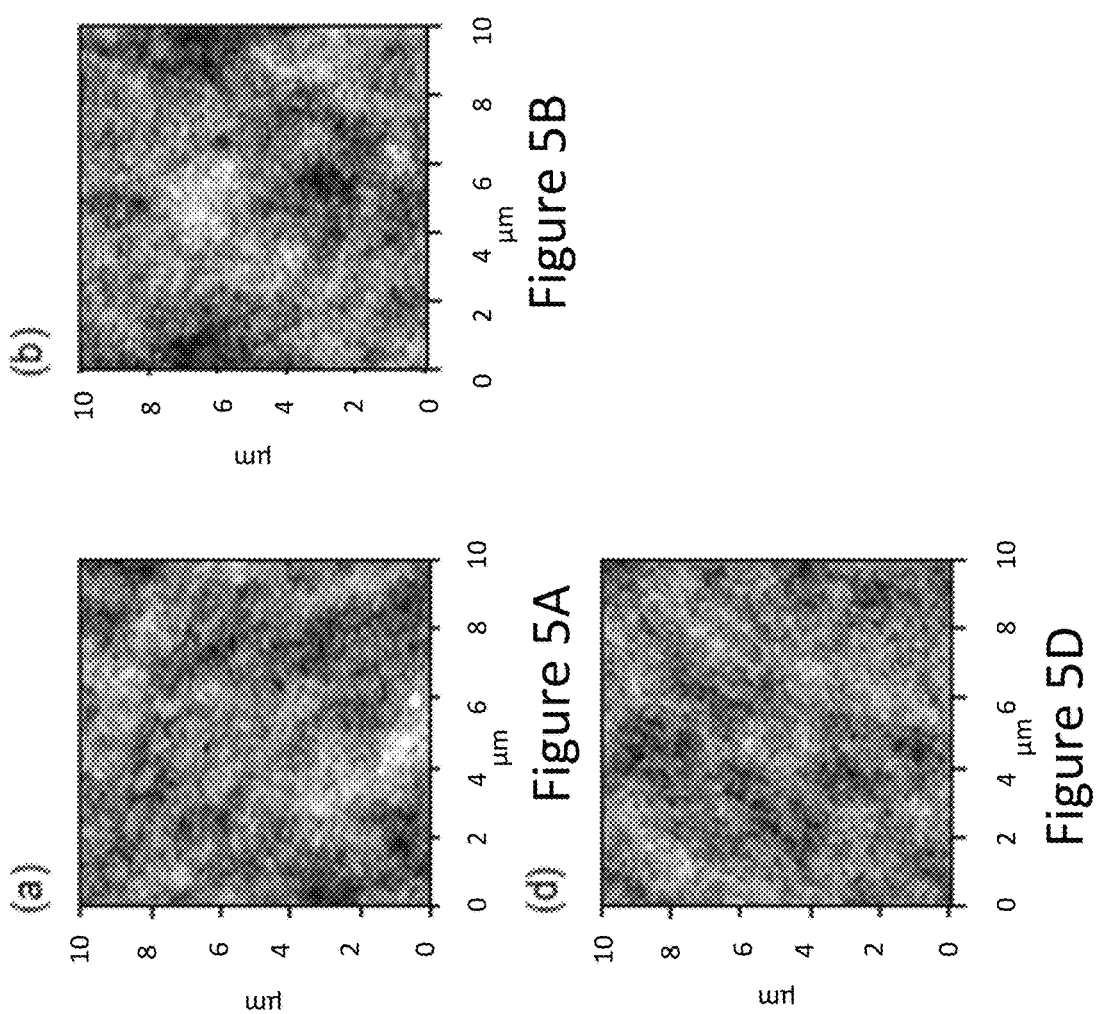
FIGS. 5A-5D. Atomic Force Microscope (AFM) tomography images of PCBM films doped with 0.1 mol % (FIG. 5A), 1 mol % (FIG. 5B), 10 mol % of 2TBD-C10 (FIG. 5C); and a pristine PCBM film (FIG. 5D).
Figure 6A:
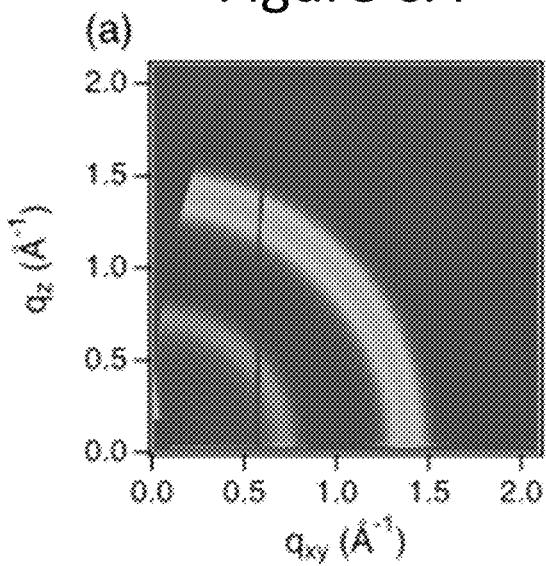
FIGS. 6A-6D. 2-Dimensional grazing incident wide angle X-ray scattering (GIWAXS) images of pristine PCBM (FIG. 6A), PCBM with 10 mol % 2TBD-C10 (FIG. 6B), PCBM with 10 mol % Me-TBD (FIG. 6C), and PCBM with 10 mol % iPr-TBD (FIG. 6D).
Figure 6B:
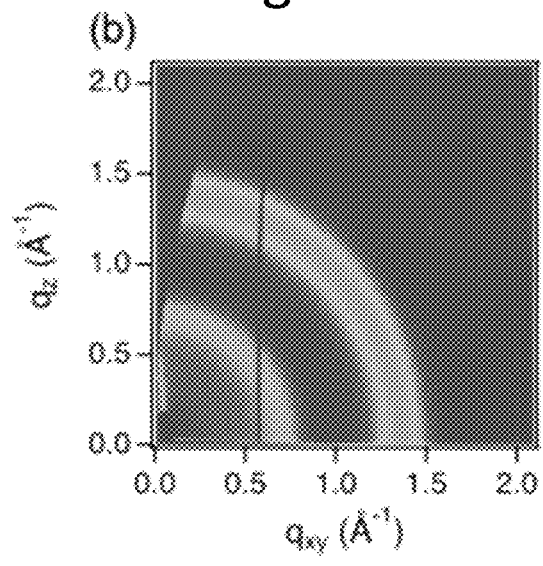
Figure 6C:
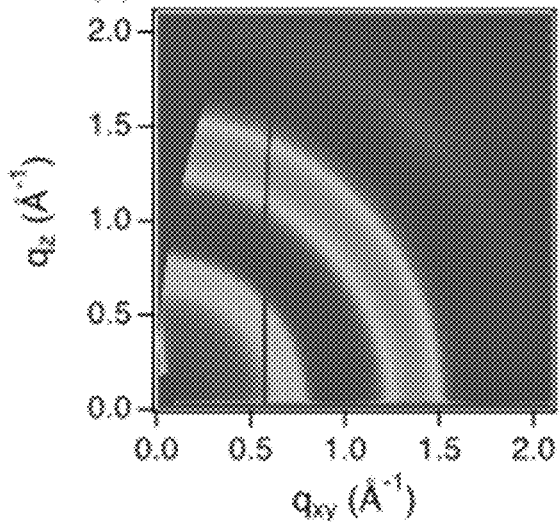
Figure 6D:
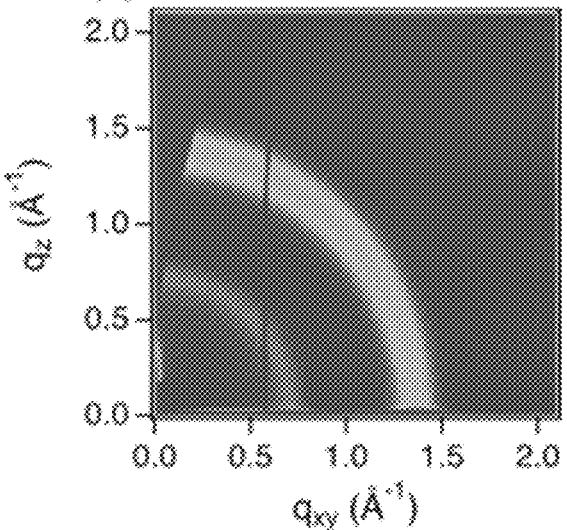
Figure 7:
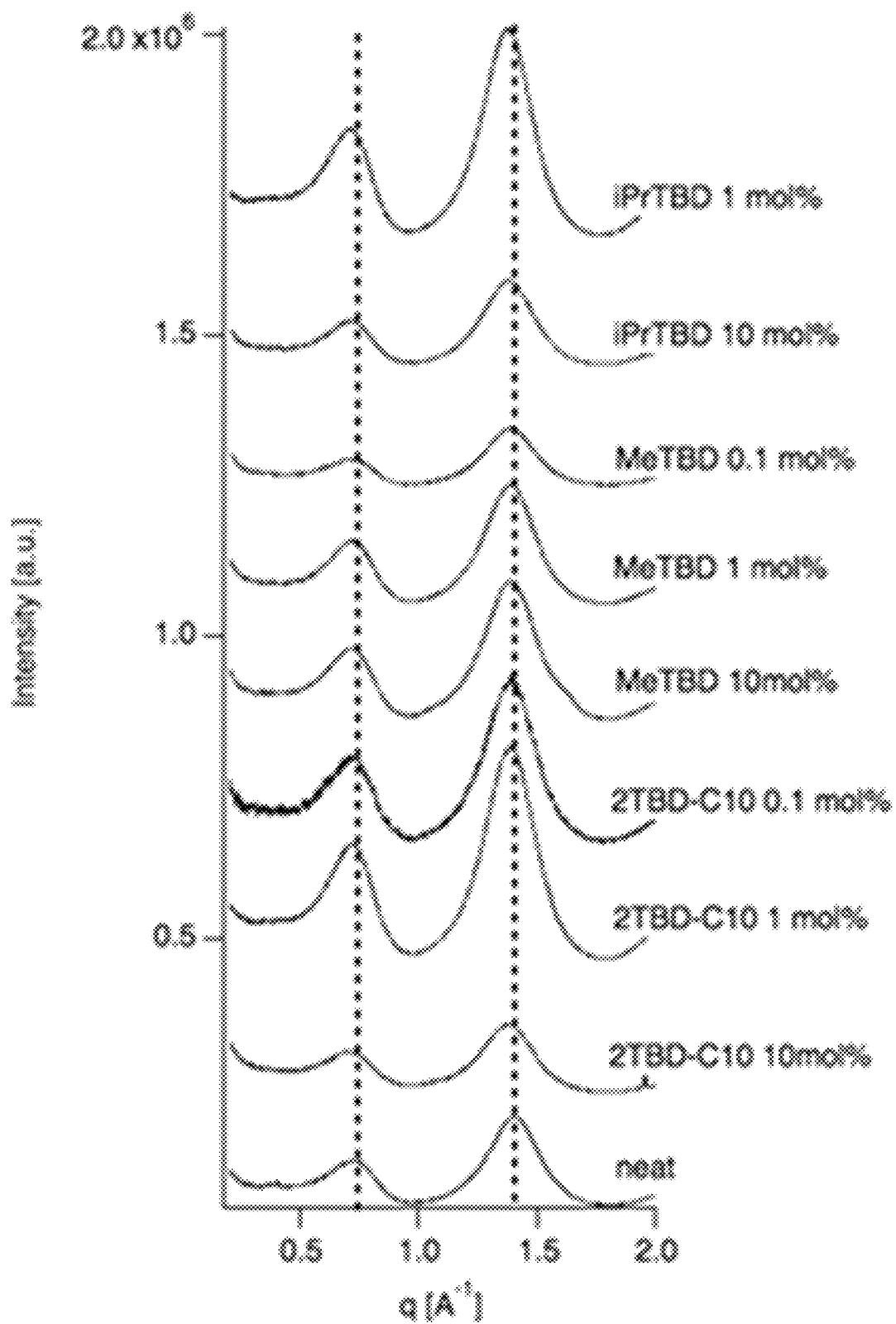
FIG. 7. GIWAXS line cuts of undoped and doped PCBM films. Dashed lines are for eye guidance.
Figure 9A:
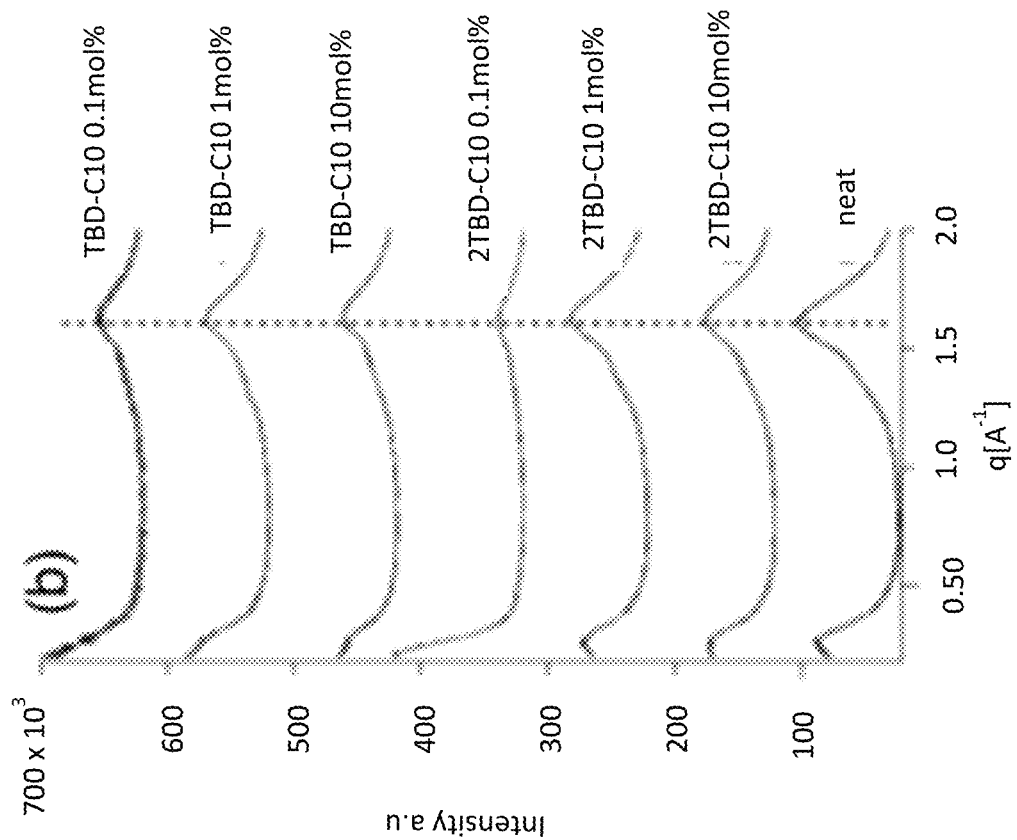
FIGS. 9A-9B. GIWAXS line cuts of undoped and doped P(NDI2OD-T2) films along in-plane (FIG. 9A) and out-of-plane (FIG. 9B) directions. Dashed lines are for eye guidance.
Figure 9B:
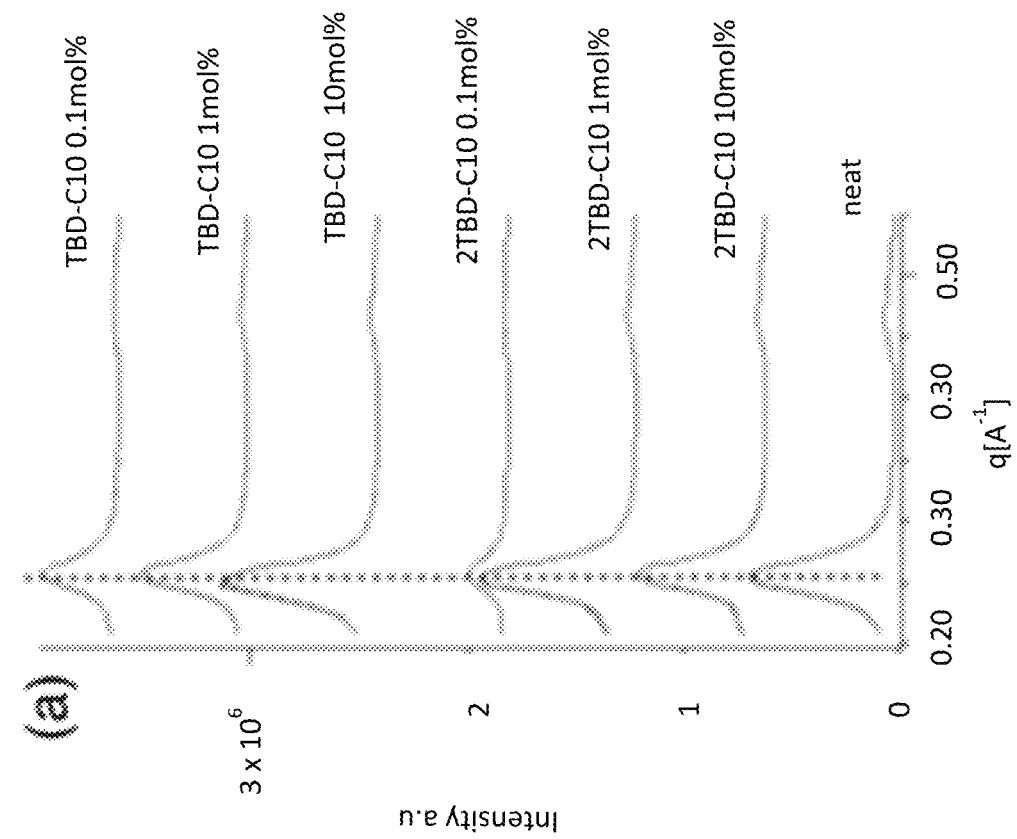

In-plane conductivities of doped PCBM films indicate that, among the TBD, DBU, and TBD derivatives synthesized herein, 2TBD-C10 gives the best conductivity throughout the 0.1 to 10 mol % doping ratio range (FIG. 4, Table 1). The conductivities of the films are $1.8 \times 10^{-4}$, $3.5 \times 10^{-3}$, and $6.5 \times 10^{-2}$ S/cm with 0.1, 1, and 10 mol % TBD unit ratio to PCBM, respectively. The trend fits well to a simple power law ($y=y_0+Ax^\alpha$) with α of 1.27. It is notable that the doping efficiency of 2TBD-C10 to PCBM films is as high as that of (2-Cyc-DMBI)$_2$: the maximum conductivity of (2-Cyc-DMBI)$_2$ doped PCBM films is reported to be $4.7 \times 10^{-3}$ S/cm at 10 mol % addition.[4] The high doping efficiency of 2TBD-C10 can partly be explained by its good miscibility with PCBM. The AFM topography images of doped PCBM films (FIG. 5a-c) show no aggregation or phase separation for each concentration and look similar to that of a pristine PCBM film (FIG. 5d).

TABLE 1

Conductivities (S/cm) of doped PCBM films

| TBD unit ratio (mol %) | DBU | TBD | Me-TBD | iPr-TBD | TBD-EH | TBD-C10 | TBD-Cylic-C4 | 2TBD-C10 |
|---|---|---|---|---|---|---|---|---|
| 0.1 | $4.9 \times 10^{-7}$ | $1.8 \times 10^{-6}$ | $4.5 \times 10^{-5}$ | $3.7 \times 10^{-7}$ | $2.7 \times 10^{-6}$ | $1.7 \times 10^{-5}$ | $1.1 \times 10^{-6}$ | $1.8 \times 10^{-4}$ |
| 1 | $2.9 \times 10^{-4}$ | $6.9 \times 10^{-5}$ | $6.2 \times 10^{-4}$ | $6.5 \times 10^{-5}$ | $9.7 \times 10^{-4}$ | na* | $2.2 \times 10^{-6}$ | $3.5 \times 10^{-3}$ |
| 10 | $6.2 \times 10^{-3}$ | $1.5 \times 10^{-3}$ | $2.4 \times 10^{-2}$ | $1.2 \times 10^{-3}$ | na* | na* | $8.1 \times 10^{-5}$ | $6.5 \times 10^{-2}$ |

*The films were not obtained due to dewetting.

Comparing monomer TBDs, we found that the advantage of substituting 7-position with an alkyl group, as the Me-TBD conductivity>TBD conductivity order holds true at any given concentrations. We also found that the branch point in the alkyl chain matters but the chain length does not on doping efficiency. The PCBM film doped with TBD-EH has 5-10 fold higher conductivity than the PCBM film doped with iPr-TBD at 0.1 and 1 mol % doping ratio, and, at 1 mol %, the conductivity is as high as that given by the film doped with Me-TBD, The conductivities of 0.1 mol % doped TBD-C10 films and Me-TBD films are nearly identical as well. A branch at C1 position should inhibit close contact between the TBI) core and the fullerene core, which is necessary to establish sufficient charge transfer.

PCBM films doped by 2TBD-C10 are more tolerant to thermal annealing than those doped with TBDs with short side chains, due to increased boiling point and thermal stability. The conductivity of the 1 mol % 2TBD-C10 doped PCBM film increased from $3.5 \times 10^{-3}$ to $7.4 \times 10^{-3}$ S/cm after thermal annealing on a hot plate in nitrogen at 150° C. for 30 min, whereas that of Me-TBD doped film's conductivity dropped from $6.2 \times 10^{-4}$ to $5.6 \times 10^{-5}$ S/cm under the same treatment. Better thermal tolerance is advantageous since it can expand thermal parameters in fabrication processes and enhance stability during operation in increased temperature.

2TBD-C10 efficiently dopes other "n-type" organic semiconductors as well. A film comprising P(NDI2OD-T2), a well-studied naphthalenediimide based conjugated polymer with high mobility,[6] doped with 2TBD-C10 has a conductivity of $7.0 \times 10^{-4}$ S/cm with 10 mol % TBD unit (Table 2). This value is comparable with P(NDI2OD-T2) doped with (2-Cyc-DMBI)$_2$ ($2.8 \times 10^{-3}$ S/cm with 11 mol %)[4] and P(NDI2OD-T2) doped with N-DMBI ($8 \times 10^{-4}$ S/cm with 10 mol %).[5] In contrast, P(NDI2OD-T2) doped with TBD-C10 has three order of magnitude lower conductivity ($1.5 \times 10^{-7}$ S/cm) in 10 mol % doping. 2TBD-C10 also dopes ITIC, an acceptor-donor-acceptor type non-tiallierene acceptor for organic photovoltaics, yielding conductivities of $4.3 \times 10^{-6}$ and $1.7 \times 10^{-6}$ S/cm with 10 and 1 mol % doping, respectively. These relatively low conductivities are partly due to lower mobility of ITIC (~$10^{-4}$ cm$^2$/Vs at space-charged limit current (SCLC))[8] than that of PCBM ($3 \times 10^{-3}$ cm$^2$/Vs at SCLC).[9]

TABLE 2

Conductivities of doped P(NDI2OD-T2) and ITIC

| | 2TBD-C10 10 mol % | 2TBD-C10 1 mol % | 2TBD-C10 0.1 mol % | TBD-C10 10 mol % |
|---|---|---|---|---|
| P(NDI2OD-2T) | $7.0 \times 10^{-4}$ | $2.4 \times 10^{-6}$ | na* | $1.5 \times 10^{-7}$ |
| ITIC | $4.3 \times 10^{-6}$ | $1.7 \times 10^{-6}$ | na* | na** |

*Too low to measure
**The films were not obtained due to dewetting.

e. Morphology

Often overlooked is the dopant's effect on film morphology. In electron transport layers (ETLs) for perovskite solar cells, for example, it is critical that the OSC layer maintains smooth coverage of the perovskite layer and good contacts to the electrodes, while allowing sufficient diffusion of the dopant. Thinking along these lines, it is possible that preferential pairings exist between dopant and OSC architectures. To date, however, there have been few reports (one report to our knowledge) exploring the morphological properties of a single family of dopants.[5]

We measured grazing incident wide angle X-ray scattering (GIWAXS) to examine short range order of the doped PCBM and P(NDI2OD-T2) thin films. The scattering patterns of PCBM films without dopant and with 10 mol % of 2TBD-C10, Me-TBD, and iPr-TBD are almost identical (FIGS. 6 (2D) and 7 (line cut)). They have two rings at around q=0.7 and 1.4 Å$^{-1}$ with full width at half maximum (FWHM) of about 0.20 and 0.15 Å$^{-1}$, respectively, indicating those films are amorphous as typically seen in fullerene films. We found that the peaks shift slightly toward lower q range by ~0.03 Å$^{-1}$ upon doping, but the impact of this change is negligible to the structural and electronic properties, given the large FWHM of the peaks. We do not observe any new peaks upon doping with 2TBD-C10, a solid dopant, corroborating the idea of molecularly mixing of the compound with PCBM.

The scattering patterns of P(NDI2OD-T2) are also insensitive to doping with 2TBD-C10 and TBD-C10 (FIGS. 8 (2D) and 9 (line cut)). The scattering pattern of pristine P(NDI2OD-T2) show a π-staking feature at 1.6 Å$^{-1}$ in the out-of-plane direction and alkyl stacking features at 0.25 and 0.47 in the in-plane direction, indicating a face-on orientation of its crystalline moieties. Addition of 2TBD-10 or TBD-C10 does not result in a notable shift of the polymer originated peaks or appearance of new peaks. We thus conclude that the crystalline moieties of the polymer are impenetrable to these TBD dopants, and the dopants reside in the amorphous moieties without forming crystallites. This conclusion is not unique to the TBD dopants but also holds true for conventional dopants such as N-DMBI as reported in[5].

f. Solar Cell Performance

Figure 10A:
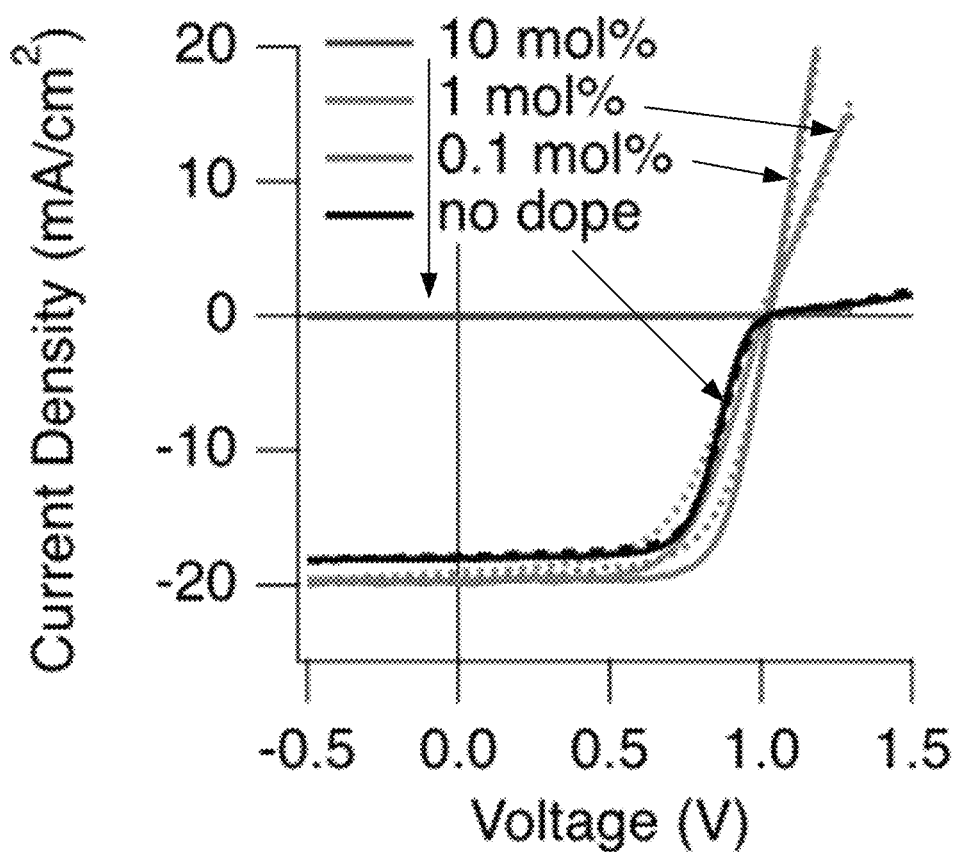
FIG. 10A. Current density-voltage (J-V) characteristics (current density in milliamps per centimeter square as a function of voltage between the cathode and anode) of a solar cell having a light absorbing region comprising methylammonium lead triiodide (MAPbI$_3$) and an electron transport layer (ETL) comprising PCBM doped with 2TBD-C10 in a ratio of (orange) 0.1 mol %, (green) 1 mol % and (purple) 10 mol %. Dashed lines represent forward scans, while solid lines reverse scans. Device structure is ITO/PTAA/MAPbI$_3$/ETL (0-10% dopant)/Ag.

We fabricated solar cells having an inverted structure and comprising a light absorbing active region comprising methylammonium lead triiodide (MAPbI$_3$) and using 2TBD-C10 doped PCBM as the electron transport layer (ETL), to assess the impact of doping to device performances (FIG. 10A). The device stack is glass/ITO (20 Ω/sq)/polytriarylamine (PTAA, ~5 nm)/MAPbI$_3$ (~400 nm)/PCBM (~100 nm)/Ag (80 nm). The results clearly show that doping with 2TBD-C10 improves the photovoltaic performance using an optimized doping ratio. The devices without doping have a photovoltaic conversion efficiency (PCE) of 11.8% with a s-kink around the open circuit voltage (V$_{OC}$) condition (J=0 mA/cm$^2$) and a good value for short circuit current J$_{SC}$ (18.0 milliamps per centimeter square In which is a sign of an electron injection barrier at the Ag/PCBM interface due to Schottky barrier formation. When the carrier concentration of PCBM is increased with 0.1 mol % of 2TBD-C10, the skink disappears by reducing the barrier width, giving a PCE of 14.5% with improved fill factor (FF) of 0.71. However, further addition of the dopant deteriorates the device performance. With 1 mol % of doping, FF is reduced to 0.61 while retaining the V$_{OC}$ and J$_{SC}$, yielding a PCE of 12.3%. With 10 mol %, the J$_{SC}$ is almost entirely quenched. We reported[10] the impact of n-dopant on the surface of MAPbI$_3$, showing that excessive surface doping decomposes MAPbI$_3$ surface by inducing release of iodine. It is likely that similar degradation happens in the highly doped devices, increasing the resistance at the MAPbI$_3$/PCBM interface and blocking charge extraction from the bulk of the active layer.

Figure 10B:
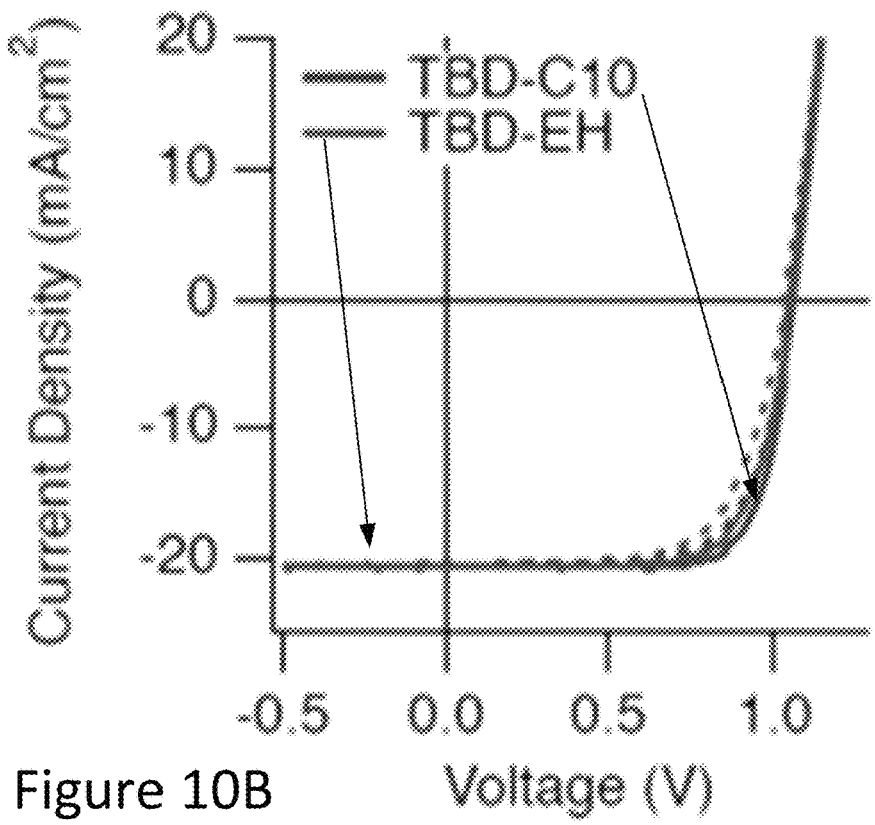
FIG. 10B. J-V characteristics of a perovskite solar cell having a light absorbing region comprising methylammonium lead triiodide (MAPbI$_3$) and an ETL comprising PCBM doped with 1% TBD-C10 or TBD-EH. Dashed lines represent forward scans, while solid lines reverse scans. Device structure is ITO/PTAA/MAPbI$_3$/ETL (0-10% dopant)/Ag.
Figure 10C:
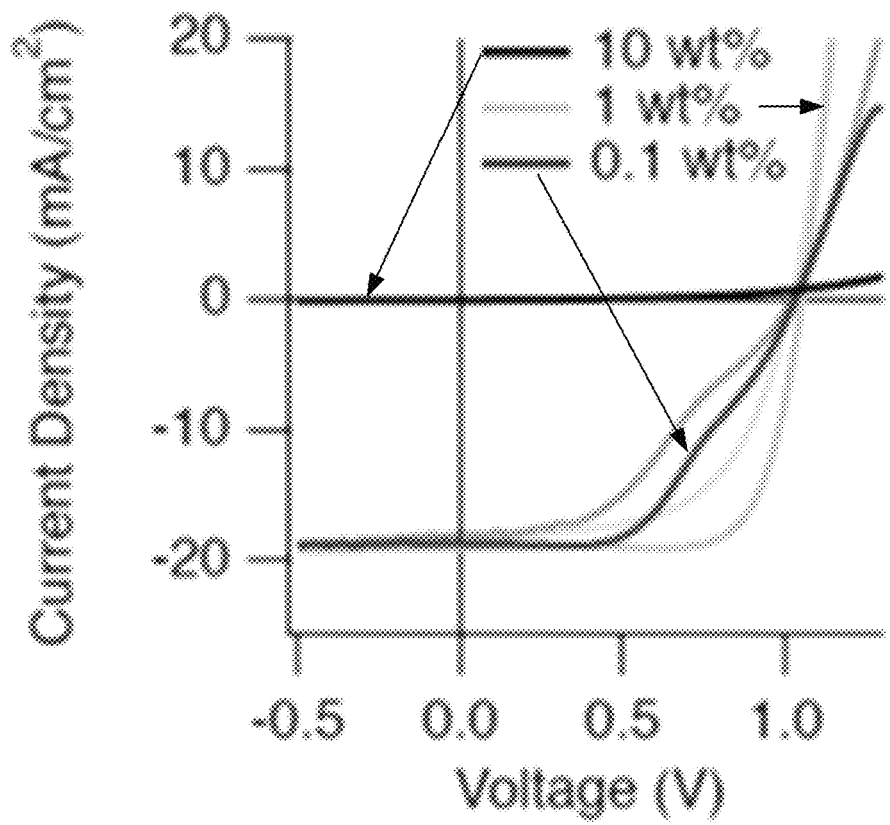
FIG. 10C. J-V characteristics of a solar cell having a light absorbing region comprising methylammonium lead triiodide (MAPbI$_3$) and an electron transport layer (ETL) comprising ITIC doped with Me-TBD (black 10 wt % MeTBD, yellow 1 wt % Me-TBD, and blue 0.1% wt % Me-TBD).

TBD-C10, TBD-EH doped PCBM and Me-TBD doped ITIC work well as an ETL in perovskite solar cells as well. Improved device J$_{SC}$, FF and PCE were achieved with optimized dopant concentration (Table 3 and FIG. 10B, 10C).

TABLE 3

Device parameters of MAPbI$_3$ based photovoltaics.

| Dopant (mol %) | ETL | VOC (V) | JSC (mA/cm2) | FF | PCE (%) |
|---|---|---|---|---|---|
| 0 (not doped) | PCBM | 1.02 | 18.0 | 0.64 | 11.8 |
| 0.1 (2TBD-C10) | PCBM | 1.02 | 19.9 | 0.71 | 14.5 |
| 1 (2TBD-C10) | PCBM | 1.01 | 19.6 | 0.61 | 12.3 |
| 10 (2TBD-C10) | PCBM | ~0.2 | <0.01 | ~0.2 | <0.1 |
| 1 (TBD-C10) | PCBM | 1.06 | 20.6 | 0.75 | 16.5 |
| 1 (TBD-EH) | PCBM | 1.05 | 20.5 | 0.72 | 15.6 |
| 0.1 (Me-TBD) | ITIC | 1.03 | 18.7 | 0.50 | 9.8 |
| 1 (Me-TBD) | ITIC | 1.05 | 19.0 | 0.73 | 14.8 |

Figure 11A:
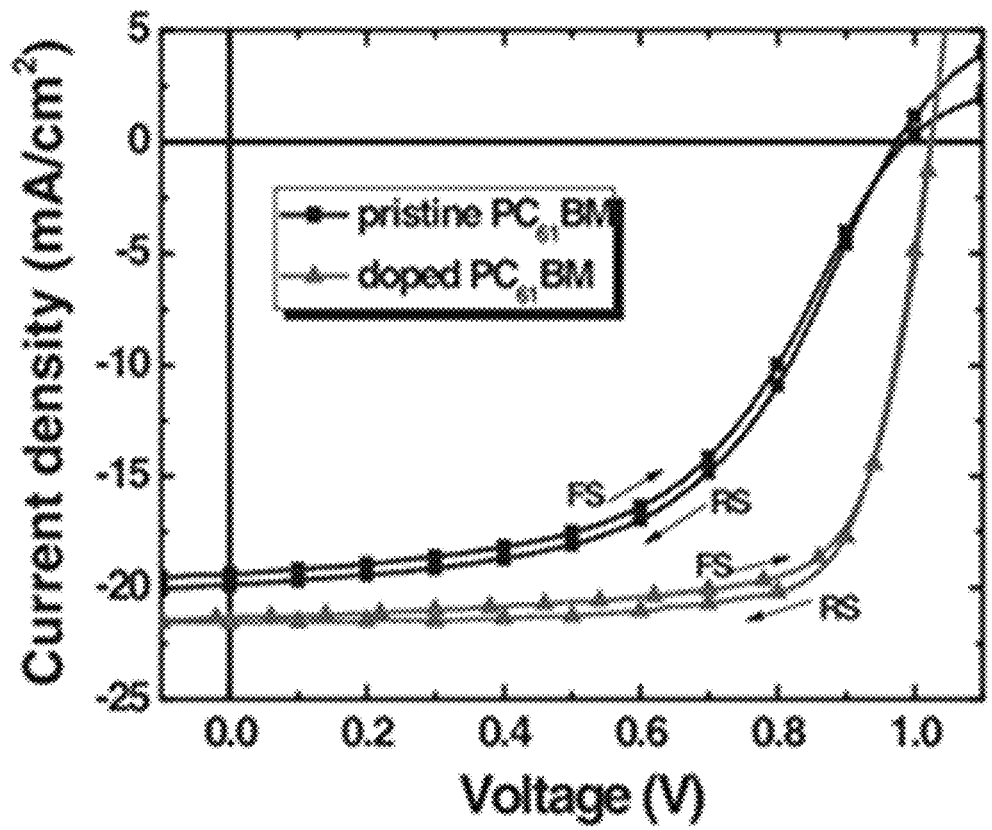
FIGS. 11A-11B compare performance of the guanidine-type n-type dopant in a solar cell (according to one or more embodiments) with performance of an amidine (DBU) type n-type dopant in a solar cell [6], showing (FIG. 11B) the guanidine based dopant successfully doped PCBM so that a solar cell including PCBM doped with guanidine as an electron transporting layer (ETL) has comparable short circuit current (Isc) and fill factor (FF) as compared to the solar cell having a PCBM ETL doped with an amidine (FIG. 11A, taken from[6]). The structure of the measured devices in both cases is glass/ITO/PTAA/MAPbI$_3$ (400 nm)/PCBM+dopant (1 mol %)/Ag (100 nm).
Figure 11B:
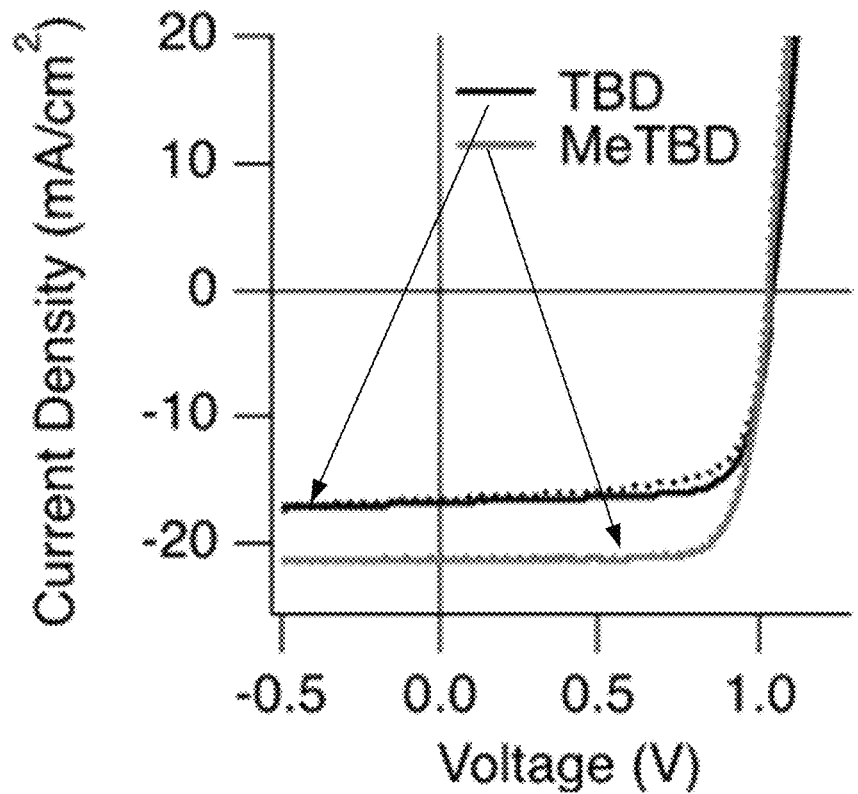

FIG. 11B shows the guanidine based dopant TBD and Me-TBD successfully doped PCBM so that a solar cell including the PCBM doped with guanidine as an electron transporting layer (ETL) has increased short circuit current (I$_{SC}$) and fill factor (FF) as compared to the solar cell having a PCBM ETL doped with an amidine (FIG. 11A, taken from[6])

g. Additional Method and Characterization Information Used to Fabricate and Characterize the Example Compounds (i) General Methods 1,5,7-Triazabicyclo[4.4.0]dec-5-ene (TBD) and 7-methyl-1,5,7-triazabicyclo[4.4.0]dec-5-ene (Me-TBD) were purchased from Aldrich Chemical and used without further purification. All manipulations involving air-sensitive reagents were performed under an atmosphere of dry argon. $^1$H and $^{13}$C NMR spectra were recorded on a Varian Inova600 spectrometer. Thermal gravimetric analysis was performed on a TA Discovery TGA under nitrogen. The mass spectroscopic data were obtained at the UCSB mass spectrometry facility on a Waters Micromass LCT Premier mass spectrometer operating in W mode, using polyethylene glycol as an internal standard. Electrochemical measurements were carried out in 0.1 M tetrabutylammonium hexafluorophosphate in dry, degassed dichloromethane with platinum wires as the working and counter electrodes and silver wire as a pseudo-reference electrode. A ferrocene-ferrocenium (Fc/Fc+) redox couple was used as an internal standard and its redox potential assumed to be −4.80 eV below vacuum level.

(ii) Synthesis

2TBD-C10: Dry THF (50 mL) was loaded into a flame-dried 250 ml schlenk flask under argon, followed by NaH (0.115 g, 4.90 mmol) and 1,5,7-triazabicyclo[4.4.0]dec-5-ene (TBD, 0.507 g, 3.59 mmol). The reaction mixture was stirred for 4 hours, after which was added 1,10-dibromodecane (0.489 g, 1.63 mmol) under positive pressure. The reaction was stirred at room temperature overnight under argon. The slightly turbid, fawn colored reaction mixture was filtered and rinsed with DCM. The filtrate was reduced in vacuo to afford a white, waxy solid. The product was purified by trituration by dissolving the product in small amounts of hexane (3×5 mL), decanting and combining the fractions. The solvent was removed in vacuo to afford 2TBD-C10 as a white powdery solid (0.591 g, 88% yield). $^1$H NMR (600 MHz, CDCl$_3$) δ 3.38 (t, J=5.5 Hz, 4H), 3.35 (m, br, 4H), 3.15 (t, J=5.5 Hz, 8H), 3.10 (m, 4H), 1.94 (t, J=5.9 Hz, 4H), 1.83 (t, J=5.5 Hz, 4H), 1.52 (m, hr, 4H), 1.27 (m, br, 12H) ppm; $^{13}$C NMR (150 MHz, CDCl$_3$) δ 151.0, 48.6, 48.5, 45.4, 43.58, 43.56, 43.51, 29.6, 29.5, 27.5, 27.0, 23.0 ppm; HRMS (ESI-TOF) m/z 417.3709 [M+H]$^+$ (calculated for C24H44N6H$^+$ [M+H]$^+$=417.3706).

iPr-TBD: Using a similar procedure as described above, NaH (0.133 g, 5.56 mmol), TBD (0.516 g, 3.71 mmol), and 2-bromopropane (1.04 mL, 11.1 mmol) were reacted to afford a yellow oil. The product was triturated with small amounts of THF or methyl tert-butyl ether (5×2 mL), decanting and combining the fractions. The solvent was removed in vacuo to afford iPr-TBD as a viscous, yellow oil (0.183 g, 27% yield). $^1$H NMR (600 MHz, CDCl$_3$) δ 4.68 (s, br, 1H), 3.44 (t, J=5.7 Hz, 2H), 3.23 (t, J=5.8 Hz, 2H), 3.20 (t, J=6.0 Hz, 2H), 3.15 (t, J=5.7 Hz, 2H), 1.97-1.90 (m, 4H), 1.16 (d, J=6.6 Hz, 6H) ppm; $^{13}$C NMR (150 MHz, CDCl$_3$) δ 150.6, 48.6, 47.6, 47.5, 39.2, 37.7, 21.8, 21.1. 19.6 ppm; HRMS (ESI-TOF) m/z 182.1655 [M+H]$^+$ (calcd for C10H19N3H$_+$ [M+H]$^+$=182.1657).

C10-TBD: Using a similar procedure as described above, NaH (0145 g, 6.05 mmol), TBD (0.613 g, 4.40 mmol), and 1-bromodecane (0.32 mL, 1.55 mmol) were reacted to afford a yellow oil. The product was purified by dissolving it in hexane (25 mL) and washing thoroughly with water (3×25 mL) to remove unreacted TBD. The organic fraction was dried over Na$_2$SO$_4$, filtered, and reduced in vacuo to afford C10-TBD as a light yellow oil (0.338 g, 78% yield). $^1$H NMR (600 MHz, CDCl$_3$) δ 3.42 (m, br, 4H), 3.21-3.14 (m, 6H), 1.97 (t, J=5.9 Hz, 2H), 1.87 (t, J=5.6 Hz, 2H), 1.55 (t, J=6.8 Hz, 2H), 1.25 (m, br, 14H), 0.87 (t, J=7.0 Hz, 3H) ppm; $^{13}$C NMR (150 MHz, CDCl$_3$) δ 150.9, 49.1, 48.5, 48.2, 45.6, 42.3, 31.9, 29.60, 29.59, 29.55, 29.3, 27.4, 26.9, 22.63, 22.55, 22.46, 14.1 ppm; HRMS (ESI-TOF) m/z 280.2753 [M+H]+ (calcd for C17H33N3H+ [M+H]+–280.2762).

(iii) Film Fabrication

Thin film samples were deposited on quartz substrates by spin-coating in a N$_2$-filled globe box (O$_2$ and water concentrations were below 0.1 parts per million (ppm)). Before spin-coating, the substrates were washed with detergent, deionized water, acetone, and isopropylalcohol in a sonication bath, then treated with air-plasma under 300 mbar for 10 min. Organic semiconductor (OS) and dopant were dissolved in chlorobenzene at 20 mM. Dopant solutions of 2 mM and 0.2 mM were also prepared by diluting the 20 mM solutions. OS solutions were stirred at 60-75° C. overnight and filtered through a 0.45 μm pore sized polytetrafluoroethylene (PTFE) filter, while dopant solutions were not heated and filtered. A OS solution and a dopant solution were mixed at a ratio of 10:1 to obtain a 0.1, 1.0 or 10 mol % doped OS solution. The doped solutions were spin-coated at 1000 rpm for 30 s within 30 min after mixture without heating. P(NDI2OD-T2) films were annealed on a hot plate at 150° C. for 60 min under nitrogen. PCBM films were not annealed. The film thicknesses measured with a profilometer (Dektak XT) and they were 30-80 nm.

(iv) Conductivity Measurement

Gold electrical contact with a thickness of 80 nm was thermally evaporated onto the films though a shadow mask. Each channel has four electrode bars of 10 mm width. The distances of the bars from the side bar were 0.2, 0.5, and 0.8 mm. In-plane conductivity were measured by Keithley 6487 Picoammeter with the two-point probe method. Resistances were measured with three distances and plotted against distance/width. The sheet resistance was obtained by the least-square fit of the linear trend. The conductivity was then calculated by dividing the sheet resistance by the thickness.

(v) Grazing Incidence X-Ray Scattering

Grazing incidence X-ray scattering experiments were conducted at the Advanced Light Source at beamline 7.3.3. The energy of the incident beam was at 10 keV, and a Pilatus 2 M area detector was used. The X-ray scattering data were taken at incidence angles of 0.15° with 2-30 s exposure times. The samples were kept under helium environment during X-ray exposure to minimize air scattering and sample degradation. The collected data were processed using Nika, a 2D data reduction macro on Igor Pro (Wave Metrics) using established procedures. A diffraction pattern from silver behenate was used to calibrate the beam center and the sample-to-detector distance. 1D profiles were created by plotting intensities along the line cuts near q$_{xy}$=0 and q$_z$=0, with a correction for the grazing incidence geometry.

(vi) Photovoltaics Fabrication

Glass substrates covered by Indium Tin Oxide (IT(i)) (University Wafers) were sonicated in acetone and then isopropyl alcohol for 10 min each. The substrates were further cleaned with air-plasma under 300 mTorr. All of the processes hereafter were conducted under nitrogen. A 2 mg/mL solution of polytriarylamine (PTAA, Aldrich) in chlorobenzene (Aldrich) were spun-coat on the substrates at 6000 rpm. A MAPbI$_3$ precursor solution was formulated by dissolving a 1/1/1 (mol/mol/mol) mixture of methylammonium iodide (Dysol), lead iodide (Aldrich) and dimethyl sulfide (Aldrich) in anhydrous DMF (Aldrich). The DMF solution was spun coat on the PTAA layer at 1000 rpm for 10 s then 4000 rpm for 30 s. When 8 s passed after the spin turned 4000 rpm, 0.2 mL of anhydrous chlorobenzene (Aldrich) was dropped on the substrate. The films were transferred on a hotplate of 100° C. immediately, and thermally annealed for 10 min. A solution for the ETL layer (30 mg/mL PCBM with 0-10% of dopants in chlorobenzene) were spun coat on the MAPbI$_3$ layer at 1000 rpm, optionally followed by a spin-coat of PEIE in isopropyl alcohol (0.02 wt %, diluted from 37% aqueous solution of PEIE from Aldrich) at 6000 rpm. The devices were finally capped with Ag (80 nm) by vacuum deposition.

(vii) Photovoltaics Characterization

The J-V characteristics were measured at 1 sun illumination (AM 1.5G, 100 mW/cm$^2$) in a N$_2$-filled glovebox with a solar simulator equipped with a Xenon lamp (Newport), a Keithley 2602 Source Meter and a calibrated silicon reference cell. The voltage was ramped from 1.50 V to –0.50 V then back to 1.50 V with 0.01 V step and 0.03 s delay time. The power conversion efficiency (PCE) was calculated with the following equation: PCE (%)=100×V$_{OC}$×J$_{SC}$ ×FF/P$_{inc}$ from the open circuit voltage, V$_{OC}$, the short circuit current, J$_{SC}$, the fill factor FF and the incident powder P$_{inc}$.

B. Process Steps

FIG. 14 is a flowchart illustrating a method of making a dopant and/or a device including the dopant.

Block 1400 represents obtaining a compound comprising a guanidine of the structure:

Block 1402 represents combining the compound comprising guanidine with a carbon containing organic compound R, so as to form a composition of matter of the structure:

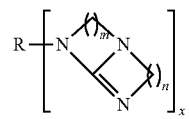

wherein:
1≤M≤8;
1≤n≤8;
2≤x≤4; and

R is any substituted or non-substituted alkyl, alkenyl, alkynyl, aryl or alkoxy group. In one or more embodiments, R can be a C$_1$-C$_{30}$ substituted or non-substituted alkyl chain, a C$_2$-C$_{30}$ substituted or non-substituted aryl chain, —(CH$_2$CH$_2$O)$_n$ (n=2~20), C$_6$H$_5$, —C$_n$F$_{(2n+1)}$ (n=2~20), —(CH$_2$)$_n$N(CH$_3$)$_3$Br(n=2~20), —(CH$_2$)$_n$N(CH$_3$)$_3$OH (n=2~20), —(CH$_2$)$_n$N(CH$_3$)$_2$ (n=2~20), —(CH$_2$)$_n$N(C$_2$H$_5$)$_2$ (n=2~20), 2-ethylhexyl, PhCmH$_{2m+1}$(m=1-20), —(CH$_2$)$_n$Si (C$_m$H$_{2m+1}$)$_3$ (m, n=1 to 20), or —(CH$_2$)$_n$Si(OSi(C$_m$H$_{2m+1}$)$_3$)$_x$ (C$_p$H$_{2p+1}$)$_y$ (m, n, p=1 to 20, x+y=3). In one or more embodiments, R is =C$_2$H$_2$=, —C$_2$H$_3$=, —C$_2$H$_4$—, —C$_2$H$_5$, =C$_3$H$_4$=, —C$_3$H$_5$=, —C$_3$H$_6$—, —C$_3$H$_7$, =C$_4$H$_6$=, —C$_4$H$_7$=, —C$_4$H$_8$—, —C$_4$H$_9$, =C$_5$H$_8$=, —C$_5$H$_9$=, —C$_5$H$_{10}$—, —C$_5$H$_{11}$, =C$_6$H$_{10}$=, C$_6$H$_{11}$=, —C$_6$H$_{12}$—, —C$_5$H$_{13}$, =C$_7$H$_{12}$=, —C$_7$H$_{13}$=, —C$_7$H$_{14}$—, —C$_7$H$_{15}$=, =C$_8$H$_{14}$=, —C$_8$H$_{15}$=, —C$_8$H$_{16}$—, —C$_8$H$_{17}$, —C$_9$H$_{16}$—, —C$_9$H$_{17}$=, —C$_9$H$_{18}$—, —C$_9$H$_{19}$, =C$_{10}$H$_{18}$=, —C$_{10}$H$_{20}$—, or —C$_{10}$H$_{21}$. One, two, three, four TBD moieties can be covalently attached to each R group.

Block 1404 represents optionally combining an acceptor with the composition of matter.

Block 1406 represents optionally solution processing the acceptor and/or composition of matter so as to form a device, such as, but not limited to, an organic solar cell, a hybrid solar cell, an organic field-effect transistor, an organic light-emitting diode, an organic photodetector or a hybrid photodetector.

FIG. 15 illustrates an example device 1500 comprising a solar cell or photodetector comprising an (e.g., transparent) anode 1502; an anode interface layer 1504; an absorbing active region 1506 (e.g., comprising organic semiconductor blends or perovskite) on the anode interface layer 1504; a cathode interface layer or electron transport layer 1508 (e.g., comprising an electron acceptor with TBD dopant) on the absorbing active region 1506; and a cathode 1510 on the cathode interface layer 1508. Cathode 1510 or anode 1502 can be on a substrate 1512.

FIG. 16 illustrates and example organic light emitting device 1600 comprising an (e.g., transparent) anode 1602; an anode interface layer 1604; an electromagnetic radiation emitting active region 1606 (e.g., comprising organic semiconductor blends) on the anode interface layer 1604; a cathode interface layer or electron transport layer 1608 (e.g., comprising an electron acceptor with TBI) dopant) on the active region 1606; and a cathode 1610 on the cathode interface layer 1608. Cathode 1610 or anode 1602 can be on a substrate 1612.

FIG. 17 illustrates and example organic transistor device 1700 comprising a channel region 1702 including the organic compound according to embodiments described herein; a source contact S to the channel region 1702; a drain contact D to the channel region 1702; a gate contact G; and a dielectric 1704 between the channel region 1702 and the gate contact G, wherein an electric field applied between the gate contact and the source contact or the drain contact modulates flow of current in the channel region between the source contact and the drain contact. The device is on a substrate 1706.

FIG. 18 illustrates an example thermoelectric device 1800 comprising an n-type region 1802 (comprising an organic compound as described herein) and p-type region between two metal layers 1804. The device 1800 operates in power generation mode when a load is connected to the device and a heat source is thermally coupled to one of the metal layers and a heat sink is thermally coupled to another of the metal layers. The device operates as a refrigerator when a bias is applied across the device.

The term "perovskite (PVSK)", as used herein refers to a material with a three-dimensional crystal structure related to that of CaTiO$_3$ or a material comprising a layer of material, wherein the layer has a structure related to that of CaTiO$_3$. The perovskite structure can be represented by the formula AMX$_3$, wherein A and M are cations of different sizes, typically A having a charge of +1 and M having a charge of +2 and X is an anion (charge −1). When A, M and X are varied, the different ion sizes may cause the structure of the perovskite material to distort away from the highly symmetric cubic structure adopted by CaTiO$_3$ to a lower-symmetry distorted structure. The symmetry will also be lower if the material comprises a layer that has a structure related to that of CaTiO$_3$. A perovskite material can be represented by the formula AMX$_3$, wherein A is at least one cation, M is at least one cation and X is at least one anion. When the perovskite comprises more than one A cation, the different A cations may be distributed over the A sites in an ordered or disordered way. When the perovskite comprises more than one M cation, the different M cations may be distributed over the M sites in an ordered or disordered way. When the perovskite comprises more than one X anion, the different X anions may be distributed over the X sites in an ordered or disordered way. In one or more optoelectronic device embodiments of the invention, the perovskite may comprise a first cation, a second cation, and at least one anion. As the skilled person will appreciate, the perovskite may comprise further cations or further anions. For instance, the perovskite may comprise two, three or four different first cations; two, three or four different second cations; and two, three or four different anions.

In one or more embodiments, A is at least one organic or inorganic cation, which may be selected from the group consisting of H$^+$, H$_3$O$^+$, NH$_4^+$, H$_3$NOH$^+$, L$^{+p}$, Na$^+$, K$^+$, Rb$^+$, Cs$^+$, Cu$^+$, Ag$^+$, BiO$^+$, methylammonium CH$_3$NH$_3^+$, ethylammonium (C$_2$H$_5$)NH$_3^+$, alkylammonium, formamidinium NH$_2$(CH)NH$_2^+$, guanidinium C(NH$_2$)$_3^+$; imidazolium C$_3$N$_2$H$_5^+$, hydrazinium H$_2$N—NH$_3^+$ (CH$_2$)$_3$NH$_2^+$, dimethylammonium (CH$_3$)$_2$NH$_2^+$, tetramethylammonium (CH$_3$)$_4$N$^+$, phenylammonium C$_6$H$_5$NH$_3^+$, arylammonium, and heteroarylammonium; In one or more embodiments, A is methylammonium CH$_3$NH$_3^+$ or formamidinium NH$_2$(CH)NH$_2^+$. M is at least one divalent metal cation, which may be selected from the group consisting of Ca$^{2+}$, Sr$^{2+}$, Cd$^{2+}$, Cu$^{2+}$, Ni$^{2+}$, Mn$^{2+}$, Fe$^{2+}$, Co$^{2+}$, Pd$^{2+}$, Ge$^{2+}$, Sn$^{2+}$, Pb$^{2+}$, Hg$^{2+}$, Yb$^{2+}$ and Eu$^{2+}$, in one or more embodiments, M is preferably Pb$^{2+}$ or Sn$^{2+}$; X is a monovalent anion, including but not limited to a halide anion F$^-$, Cl$^-$, Br$^-$, I$^-$, a cyanide CN$^-$, or a formate HCOO$^-$; X can be a single kind of anion, or comprise two, three of four different kinds of anions.

In one or more embodiments, the active layer comprises a material of the formula A$_a$B$_b$M$_m$X$_x$, wherein A represents a monovalent inorganic cation, a monovalent organic cation or mixture of different monovalent organic or inorganic cations; B represents a divalent inorganic cation, a divalent organic cation or mixture of different divalent organic or inorganic cations; M is Bi$^{3+}$ or Sb$^{3+}$; X represents a monovalent halide anion, or mixture of different monovalent halide anions; a, b represent 0 or any positive numbers, m, x represent any positive numbers, and a+2b+3m =x. In one or more embodiments, B is a divalent primary, secondary, tertiary, or quaternary organic ammonium cation with 1 to 100 carbons and 2 to 30 heteroatoms, wherein two of the heteroatoms are positively charged nitrogen atoms. In certain instances, B is selected from the group consisting of Mg$^{2+}$, Ca$^{2+}$, Sr$^{2+}$, Ba$^{2+}$, Sn$^{2+}$, Ti$^{2+}$, V$^{2+}$, Ni$^{2+}$, Cr$^{2+}$, Co$^{2+}$, Fe$^{2+}$, Cu$^{2+}$, Zn$^{2+}$, Mn$^{2+}$, Hg$^{2+}$, Ag$^{2+}$, NH$_3$CH$_2$CH$_2$NH$_3^{2+}$, $^{NH}$$_3$(CH$_2$)$_6$NH$_3^{2+}$, $^{NH}$$_3$(C$_2$)$_8$NH$_3^{2+}$, NH$_3$C$_6$H$_4$NH$_3^{2+}$ In one or more embodiments, the active layer may comprise a material selected from the group consisting of MX$_3$, AMX$_4$, A$_3$MX$_6$, A$_3$M$_2$X$_9$, perovskites, A$_2$MM'X$_6$ double perovskites, and Ruddlesden-Popper phases, wherein A represents a monovalent inorganic cation, a monovalent organic cation; A' represents a second monovalent organic or inorganic cation; M is Bi$^{3+}$ or Sb$^{3+}$; X represents a monovalent halide anion, or mixture of different monovalent halide anions. As used herein, the term "double perovskite" refers to a compound which is closely related to the perovskite AMX$_3$ compound but has a unit cell twice that of perovskite and two different metals on the M sites, so the formula can be written as A$_2$MM'X$_6$. The term "Ruddlesden-Popper phase" as used herein refers to a form of layered perovskite structures which consist of two-dimensional perovskite slabs and additional cation interlayers. The general formula of those phases can be written as A$_{n+1}$A'$_{n/2}$M$_{n/2}$X$_{3n+1}$. In certain instances, the active layer is a bismuth halide selected from the group consisting of BiI$_3$, K$_3$Bi$_2$I$_9$, Rb$_3$Bi$_2$I$_9$, Cs$_3$Bi$_2$I$_9$, (CH$_3$NH$_3$)$_3$Bi$_2$I$_9$, (NH$_2$(CH)NH$_2$)$_3$Bi$_2$I$_9$, and (NH$_3$(CH$_2$)$_2$NH$_3$)$_2$Bi$_2$I$_{10}$.

The perovskite photovoltaic device may have a standard or inverted structure. It may comprise a substrate, a first electrode deposited on the substrate, a second electrode, an electron conducting/hole blocking layer deposited either between the first electrode and the active layer, or between the active layer and the second electrode, and an optional hole conducting/electron blocking layer deposited either in between the first electrode and the active layer, or between the active layer and the second electrode.

In one or more solar cell embodiments, during operation, both the electron donor and the electron acceptor absorb photons to create electron-hole pairs, the (acceptor molecule interfacing with the donor molecule) receives the electron in the electron hole pair and transports the electron to the cathode interface layer and the cathode. The hole is transported by the donor to the anode interface layer and then the anode.

The electron transporting/conducting layer material can be selected from, but not limited to, the group comprising or consisting of TiO$_2$, ZnO, SnO$_2$, SiO$_2$, ZrO$_2$, CdSe, WO$_3$, ZnSnO$_4$, PbI$_2$, SrTiO$_3$, fullerene based electron acceptors (C$_{60}$, C$_{70}$, PC$_{61}$BM, PC$_{71}$BM, ICBA), borane based electron acceptors (3TPYMB), Bathocuproine (BCP), bathophenanthroline (Bphen), ITiC type of non-fullerene acceptors, NDI and PDI based non-fullerene acceptors, and the combination of above (double layer).

The electron transporting layer may have a thickness of 2 nm to 500 nm, preferably a thickness of 20 nm to 200 nm, more preferably a thickness of 50 nm to 100 nm.

The hole transporting/conducting layer material can be selected from, but not limited to, the group comprising or consisting of poly(3,4-ethylenedioxythiophene): polystyrene sulfonate (PEDOT:PSS), p-type organic small molecule semiconductors such as Spiro-MeOTAD, pentacene, biscarbazolylbenzene, oligomer semiconductors, polymer semiconductors such as PTAA, poly(3-hexylthiophene-2,5-diyl) (P3HT), donor-acceptor copolymer semiconductors such as PCPDTBT, PCDTBT, metal oxides such as CuI, CuBr, CuSCN, Cu$_2$O, CuO or CIS. VO$_x$, NbO$_x$, MoO$_x$, WO$_x$, NiO$_x$, where x is 3 or less than 3, or other main group or transition metal oxides and a compound as shown in FIG. 1 of U.S. Ser. No. 14/954,131.

The active layer, electron transporting/hole blocking layers, hole transporting/electron blocking layers of the electronic device may be deposited by solution casting or vapor deposition. Illustrative thin film deposition methods include a spin coating method, a casting method, a microgravure coating method, a gravure coating method, a bar coating method, a roll coating method, a blade coating method, a wire bar coating method, a dip coating method, a spray coating method, a free span coating method, a dye coating method, a screen printing method, a flexo printing method, an offset printing method, an inkjet printing method, a dispenser printing method, a nozzle coating method and a capillary coating method, for forming a film from a solution.

In one or more embodiments, the solar cell s a fill factor of more than 70%, an J$_{SC}$ over 19 mA/cm$^2$, and a PCE of greater than 14%.

Composition/Device Embodiments

The composition of matter and/or device can be embodied in many ways including, but not limited to, the following.

1. A composition of matter, comprising:
an organic compound of the structure:

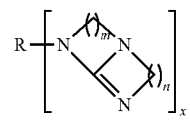

wherein:
1≤m≤8;
1≤n≤8;
2≤x≤4; and
R is any substituted or non-substituted alkyl, alkenyl, aikynyl, aryl or alkoxy group.

2. The composition of matter of embodiment 1, wherein R contains one or more heteroatoms (e.g., selected from the group comprising, but not limited to, silicon, oxygen, nitrogen, phosphorus sulfur and halides).

3. The composition of matter of embodiments 1 or 2, wherein R contains one or more aromatic moieties (e.g., comprising, but not limited to benzene or benzene derivatives, thiophene or thiophene derivatives).

4. The composition of matter of any of the preceding embodiments, wherein

is any of the following bicyclic structures:

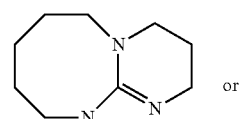 or 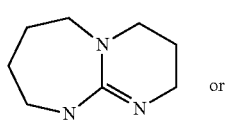 or

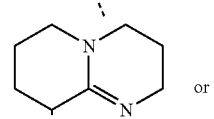 or

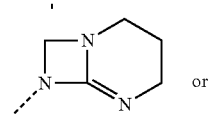 or

-continued

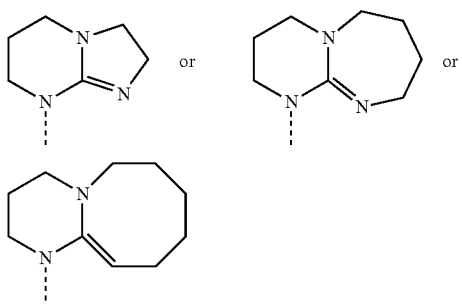

5. The composition of matter of any of the preceding embodiments, wherein the organic compound is a dimer (x=2) wherein each end of the R is connected to one of the

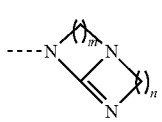

6. The composition of matter of embodiment 5, wherein the organic compound is

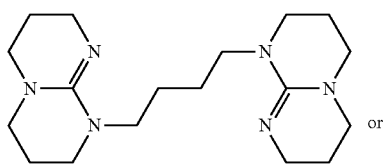

2TBD-C₄

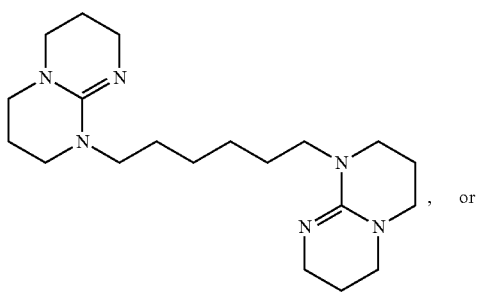

2TBD-C6

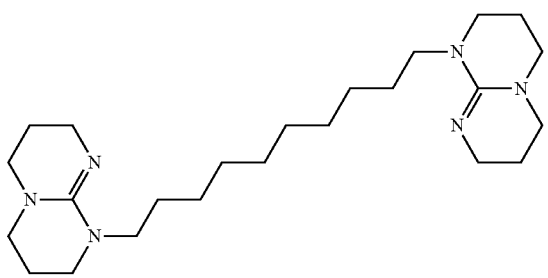

2TBD-C10

7. The composition of matter of any of the embodiments 1-4, wherein the organic compound is a trimer (x=3) wherein each end of the R is connected to one of the

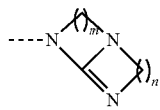

8. The composition of matter of embodiment 7, wherein the organic compound is

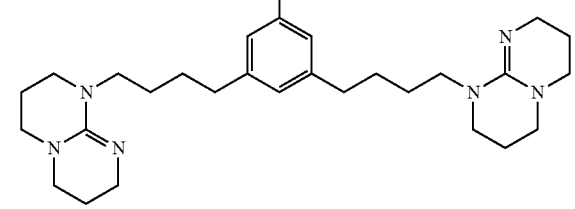

9. The composition of matter of any of the preceding embodiments bonded to a fullerene, or wherein the R comprises the fullerene, so as to n-type dope the fullerene.

10. The composition of matter of any of the preceding embodiments 1-8 bonded to a compound such as, but not limited to, a phenyl-$C_{61}$-butyric acid methyl ester (PCBM), Poly{[N,N'-bis(2-octyldodecyl)-napthalene-1,4,5,8-bis(dicarboximide)-2,6-diyl]-alt-5,5'-(2,2'-bithiophene)} (N2200) any fullerene acceptor as described in [12], any non-fullerene acceptor described in [13], the compound having mostly planar pi-conjugated core with donor and acceptor building blocks, or a material having an electron affinity of 3-5 electron volts (eV) or 3-4.5 eV, so as to n-type dope the compound.

11. The composition of matter of any of the preceding embodiments 1-8 bonded to an electron acceptor (e.g., comprising a second organic compound) so as to n-type dope the electron acceptor. Examples of the second organic compound include, but are not limited to, a fullerene (including any fullerene acceptor described in [12], PCBM, N2200, ITIC, any non-fullerene acceptor described in [13], a compound having mostly planar pi-conjugated core with donor and acceptor building blocks, or a material having an electron affinity of 3-5 eV or 3-4.5 eV.

12. The composition of matter of embodiment 1 bonded to a fullerene, or wherein the R comprises the fullerene, so as to form the composition of matter comprising or compound having the structure:

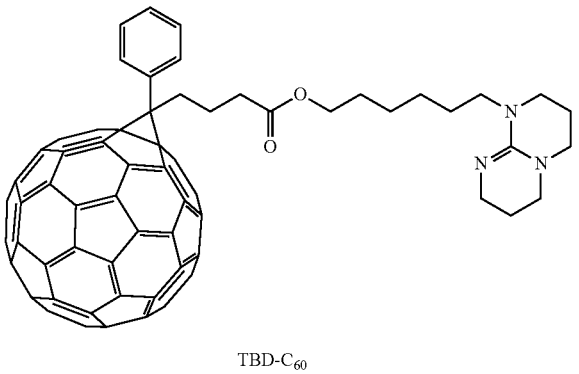

TBD-C$_{60}$

13. The composition of matter of any of the preceding embodiments, wherein the R is selected so that the organic compound is miscible with an organic acceptor. Examples of the organic acceptor include, but are not limited to, a fullerene, PCBM, N2200 or ITIC.

14. The composition of matter of embodiment 13, further comprising a single phase amorphous composition including the organic compound combined with the organic acceptor, wherein the organic compound n-type dopes the organic acceptor.

15. A device comprising the organic compounds or composition of matter of any of the embodiments 1-14, wherein the device is a light emitting device (e.g., as illustrated in FIG. 16), a light absorbing device (e.g., as illustrated in FIG. 15), a thermoelectric device (as illustrated in FIG. 18 and comprising an n-type region including the organic compound of any of the examples 1-14), or a transistor (e.g., as illustrated in FIG. 17).

16. The device of embodiment 15, further comprising an active region (including but not limited to an perovskite) or electron transporting layer (e.g., PCBM, N2200) including the organic compound or the compositions of matter.

17. The device of embodiment 16, wherein the organic compound is n-type self-doped such that the organic compound emits light in response to current (e.g., when the active region 1606 comprises the organic compound of any of the embodiments 1-14), transports current in a channel of a transistor (e.g., when the channel region 1702 comprises the organic compound of any of the embodiments 1-14), or generates current in response to light (e.g., when the active region 1506 comprises the organic compound of any of the embodiments 1-14).

18. The device of embodiment 16, wherein the active region or the electron transporting layer includes an organic acceptor combined with the organic compound so that the organic compound n-type dopes the organic acceptor.

19. The device of embodiments 15-18, wherein the organic compound is non-volatile and stable in air up to a temperature of at least 200 degrees Celsius.

20. A device, comprising:
an organic transistor 1700, an organic light absorbing device 1500, a hybrid solar cell device, a thermoelectric device 1800 (e.g., comprising an n-type region including the organic compound of any of the examples 1-14), or an organic light emitting device 1600 comprising an n-type dopant including an organic compound of the structure:

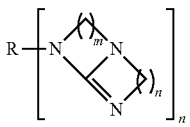

wherein:
$0 \leq m \leq 8$;
$0 \leq n \leq 8$;
$1 \leq x \leq 4$;
and R is any substituted or non-substituted alkyl, alkenyl, alkynyl, aryl or alkoxy group.

21. The device of embodiment 20, wherein R contains one or more heteroatoms.

22. The device of embodiments 20 or 21, wherein R contains one or more aromatic moieties.

23. The device of any of the embodiments 20-22, further comprising a light emitting active region including the n-type dopant.

24. The device of any of the embodiments 20-22 further comprising a light absorbing active region including the n-type dopant.

25. The device of any of the embodiments 20-22, wherein the device is a transistor further comprising a conductive channel including the n-type dopant.

26. The device or composition of matter of any of the examples 1-25, wherein a composition of R and/or a weight and/or molar ratio of the amount of the R to the amount of

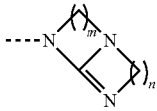

in the organic compound are selected to obtain the composition of matter (e.g., comprising/consisting essentially of a solid) having a thermal stability at or above 250° C., for example, such that the weight of the composition of matter at a temperature 270° C. under inert atmosphere (comprising <0.1% oxygen) is in a range of 90%-100% of the weight of the composition of matter at the temperature of 25° C., e.g., when the mechanism for the weight loss or decomposition includes, but is not limited to, sublimation and/or evaporation and/or thermal annealing during the device's fabrication process. In one or more examples, the weight ratio is 0.5 or less.

27. The device or composition of matter of any of the examples 1-25, wherein an overall molecular weight of the composition of matter (which is related to the molecular weight of R and the number of TBD in each molecule) and the molecular interaction (linear alkyl linker vs. branched alkyl linker) are selected to achieve the composition of matter that is thermally stable at or above 250° C., for example, such that the weight of the composition of matter at a temperature 270° C. in an inert atmosphere (comprising <0.01% oxygen) is in a range of 90%-100% of the weight of the composition of matter at the temperature of 25° C., e.g., when the mechanism for the weight loss or decomposition includes, but is not limited to, sublimation and/or evaporation and/or thermal annealing during the device's fabrication process.

28. The device or composition of matter of any of the examples 1-25, wherein the composition of R, the amount of R, the composition and/or the amount/concentration of the

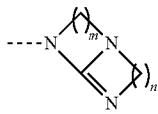

in the composition of matter are selected to obtain a miscibility and/or thermal stability of the composition of matter suitable for solution processing the composition of matter in the device.

29. The device or composition of matter of any of the examples 1-25, wherein the composition of R, the amount of R, the composition and/or the amount of the

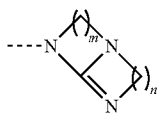

in the composition of matter are selected to obtain an oxidation potential (e.g., 1.05 V or less vs. Ag/Ag$^+$) of the organic compound suitable for n-type doping the composition of matter in the device.

30. The device or composition of matter of any of the examples 1-25, wherein the R, the second organic compound/electron acceptor have an electron affinity of 3-5 eV or 3.5-4.5 eV. If the electron affinity is too small, the composition of matter/electron acceptor may be difficult to dope. If the electron affinity is too large, the composition of matter or electron acceptor can be spontaneously doped in ambient air and is not stable.

31. The device or composition of matter of any of the examples 1-25, wherein the concentration and composition of the organic compound in the composition of matter are such that a film (solution cast in a device) comprising the composition of matter has a surface roughness less than 1 nanometer over an area of 10 microns by 10 microns.

32. The device or composition of matter of any of the examples 1-31, wherein the concentration and composition of the organic compound in the composition of matter are such that, in the composition of matter comprising the electron acceptor comprising a second organic compound doped by combination with the organic compound, the electron acceptor's crystalline structure (comprising a crystallite) is not penetrated by the organic compound and the organic compound comprises an amorphous moiety in the composition of matter.

33. The device or composition of matter of any of the examples 1-32 wherein the composition of matter comprises an amount of the organic compound in a range of 0.1 mol %-10 mol % or in a range 0.1 mol %-1 mol %, wherein mol % is the percentage that the moles of the organic compound are of the total moles that are in the composition of matter.

34. The device or composition of matter of any of the examples 1-33 wherein the n-type dopant of the electron acceptor (comprising a second organic compound combined or bonded to the organic compound in the composition of matter) consists essentially of the organic compound providing negative charge to the electron acceptor so as to increase or control an n-type conductivity of the composition of matter.

35. The device or composition of matter of any of the examples 1-34, wherein the organic compound n-type dopes the electron acceptor in the composition of matter such that the composition of matter consisting essentially of the electron acceptor combined with the organic compound has an n-type conductivity κ in a range of $1 \times 10^{-5} \le \kappa \le 1 \times 10^{-1}$ Siemens per centimeter (S/cm) or $1 \times 10^{-3} \le \kappa \le 1 \times 10^{-1}$ S/cmM.

Advantages and Improvements

Efficient and air-stable n-dopant for organic semiconductors reported so far are expensive because several synthetic steps are required to build their idiosyncratic chemical structures. In contrast, TBD derivatives according to embodiments described herein can be fabricated in one step from the TBD.

Moreover, guanidine dopants according to one or more embodiments described herein increase conductivity, shift energy levels (see FIG. 19), decrease charge-injection barriers, passivate deep electron traps, and lower recombination rates in devices. For example, doping efficiency of the TBD derivatives according to one or more embodiments is higher than for compounds such as amidine-type dopant 1,8-Diazabicyclo[5.4.0]undec-7-ene DBU[6] of the structure

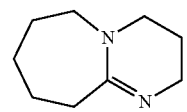 [SMILES: C1CCC2=NCCCN2CC1]

The functioning of the guanidine based organic compounds (according to embodiments described herein) as an n-type dopant is surprising and unexpected given that the HOMO levels of guanidine compounds (~5.1 eV) are largely mismatched with the LUMO levels of electron acceptors.

REFERENCES

The following references are incorporated by reference herein.

[1] B. Lüssem, C.-M. M. Keum, D. Kaseinann, B. Naab, Z. Bao, K. Leo, Chemical reviews 2016, 116, 13714.

[2] M. Bendikov, F. Wudl, D. F. Perepichka, Chem Rev 2004, 104, 4891.

[3] F. Li, A. Werner, M. Pfeiffer, K. Leo, X. Liu, J Phys Chem B 2004, 108, 17076.

[4] Naab, S. Zhang, K. Vandewal, A. Salleo, S. Barlow, S. R. Marder, Z. Bao, Adv Mater 2014, 26, 4268.

[5] B. Russ, M. J. Robb, F. G. Brunetti, L. P. Miller, E. E. Perry, S. N. Patel, V. Ho, W. B. Chang, J. J. Urban, M. L. Chabinyc, C. J. Hawker, R. A. Segalman, Adv Mater 2014, 26, 3473.

[6] L. Liu, J. Duan, X. Ma, C. Ge, Y. Jiang, F. Qin, S. Xiong, F. Jiang, B. Hu, X. Gao, Y. Yi, Y. Zhou, Adv Fund Mater 2017, 1703254.

[7] Y. Yang, Z.-G. Zhang, Bin, S. Chen, L. Gao, L. Xue, C. Yang, Y. L. J Am Chem Soc 2016, DOI 10.1021/jacs.6b09110.

[8] S. Foster, F. Deledalle, A, Mitani, T. Kimura, K. Kim, T. Okachi, T. Kirchartz, J. Oguma, K. Miyake, J. R. Durrant, S. Doi, J. Nelson, Advanced Energy Materials 2014, 4, 1400311.

[9] E. E. Perry, J. G. Labram, N. R. Venkatesan, H. Nakayama, M. L. Chabinyc, Adv Electron Mater 2018, 1800087.

[10] Chem. Phys. Lett, 1994, 224, 333-337.

[11] Chem. Phys. Lett, 1994, 220, 138-140.

[12] Ganesamoorthy et al., Fullerene based acceptors for efficient bulk heterojunction organic solar cell applications, Solar Energy Materials & Solar Cells 161 (2017) 102-148.

[13] Yan, C., Barlow, S., Wang, Z. et al. Non-fullerene acceptors for organic solar cells. *Nat Rev Mater* 3, 18003 (2018) doi.10.1038/natrevmats.201.

Conclusion

This concludes the description of the preferred embodiment of the present invention. The foregoing description of one or more embodiments of the invention has been presented, for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A composition of matter, comprising:
an organic compound of the structure:

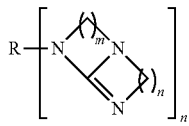

wherein:
$1 \leq m \leq 8$;
$1 \leq n \leq 8$;
$2 \leq x \leq 4$; and
R is any substituted or non-substituted alkyl, alkenyl, alkynyl, aryl or alkoxy group; and
the

comprises an n-type dopant.

2. The composition of matter of claim 1, wherein R contains one or more heteroatoms.

3. The composition of matter of claim 1, wherein R contains one or more aromatic moieties.

4. The composition of matter of claim 1, wherein:

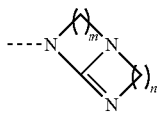

is any of the following bicyclic structures:

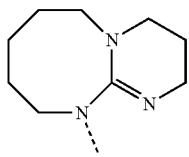 or 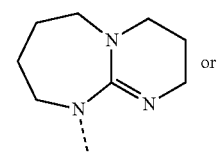 or

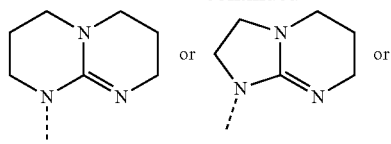

-continued

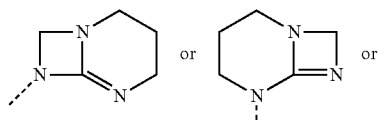

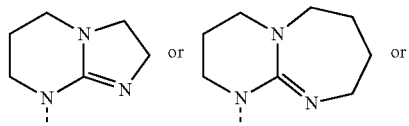

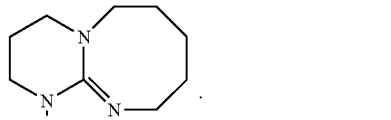

5. The composition of matter of claim 1, wherein the organic compound is a dimer (x=2) wherein each end of the R is connected to one of the

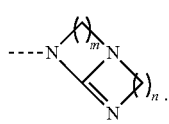

6. The composition of matter of claim 5, wherein the organic compound is

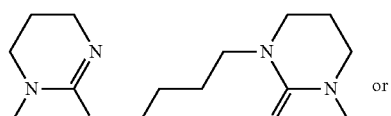 or

2TBD-C$_4$

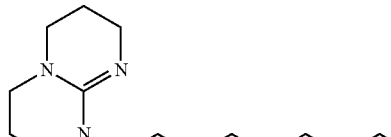 or

-continued

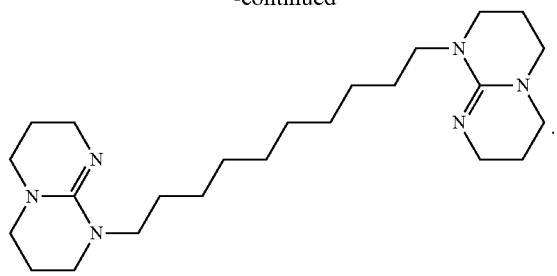

7. The composition of matter of claim 1, wherein the organic compound is a trimer (x=3) wherein each end of the R is connected to one of the

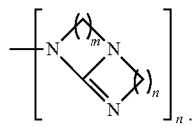

8. The composition of matter of claim 1 bonded to a phenyl-$C_{61}$-butyric acid methyl ester (PCBM), or wherein the R comprises the PCBM, so as to n-type dope the PCBM.

9. The composition of matter of claim 1 bonded to an electron acceptor, or wherein the R comprises an electron acceptor, so as to n-type dope the acceptor.

10. The composition of claim 1 bonded to a fullerene so as to form the organic compound

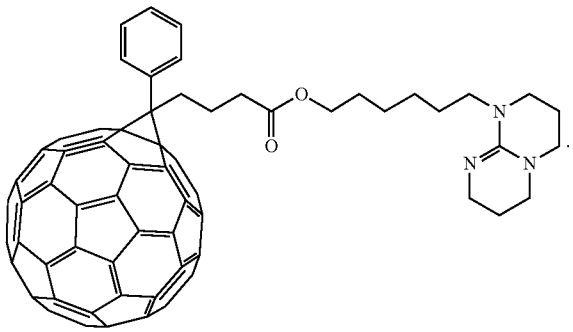

TBD-$C_{60}$

11. The composition of matter of claim 1, wherein the R is selected so that the organic compound is miscible with an organic acceptor.

12. The composition of matter of claim 11, further comprising a single phase amorphous composition including the organic compound combined with the organic acceptor, wherein the organic compound n-type dopes the organic acceptor.

13. The composition of matter of claim 1, wherein the

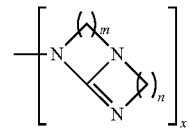

comprises an n-type dopant for the R.

14. A composition of matter, comprising an organic compound of the structure:

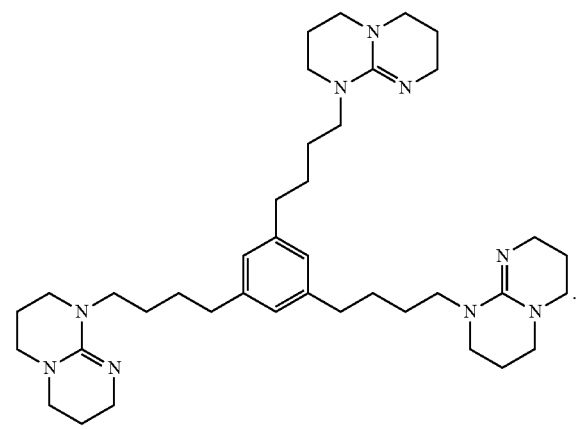 [SMILES: c1c(CCCCN2CCCN3CCCN=C23)cc(CCCCN2CCCN3CCCN=C23)cc1CCCCN1CCCN2CCCN=C12]

15. A composition of matter comprising an organic compound of the structure

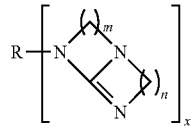

wherein:
1≤m≤8;
1≤n≤8;
2≤x≤4; and
R is any substituted or non-substituted alkyl, alkenyl, alkynyl, aryl or alkoxy group; and
the R comprises the fullerene, so as to n-type dope the fullerene.

* * * * *